US011535826B2

(12) United States Patent
Espinosa-Hoyos et al.

(10) Patent No.: US 11,535,826 B2
(45) Date of Patent: Dec. 27, 2022

(54) ENGINEERED 3D-PRINTED ARTIFICIAL AXONS

(71) Applicant: Massachusetts Institute of Technology, Cambridge, MA (US)

(72) Inventors: Daniela Espinosa-Hoyos, Cambridge, MA (US); Anna E. Jagielska, Topsfield, MA (US); Huifeng Du, Cambridge, MA (US); Nicholas X. Fang, Lexington, MA (US); Krystyn J. Van Vliet, Lexington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1268 days.

(21) Appl. No.: 15/975,452

(22) Filed: May 9, 2018

(65) Prior Publication Data

US 2018/0327715 A1 Nov. 15, 2018

Related U.S. Application Data

(60) Provisional application No. 62/504,476, filed on May 10, 2017.

(51) Int. Cl.
*C12N 5/079* (2010.01)
*G01N 33/50* (2006.01)
(Continued)

(52) U.S. Cl.
CPC .......... *C12N 5/0622* (2013.01); *B29C 64/135* (2017.08); *B33Y 70/00* (2014.12);
(Continued)

(58) Field of Classification Search
CPC .............. C12N 5/0622; C12N 2533/30; C12N 2535/00; C12N 2539/00; G01N 33/5058;
(Continued)

(56) References Cited

U.S. PATENT DOCUMENTS 9,072,592 B2 7/2015 Park et al.
9,512,404 B2 12/2016 Stupp et al.
(Continued)

FOREIGN PATENT DOCUMENTS

CN 105631930 A 6/2016
CN 105711099 A 6/2016
(Continued)

OTHER PUBLICATIONS

Liu et al. Tissue-Engineered Regeneration of Completely Transected Spinal Cord Using Induced Neural Stem Cells and Gelatin-Electrospun Poly (Lactide-Co-Glycolide). PLOS One (2015), 10(3), e0117709, 19 pages. (Year: 2015).*
(Continued)

*Primary Examiner* — Sean C. Barron
(74) *Attorney, Agent, or Firm* — Hamilton, Brook, Smith & Reynolds, P.C

(57) ABSTRACT

Materials and methods for cell-mimetics having mechanical properties of biological neural axons are provided. A cell-mimetic device includes an array of fibers comprised of hexanediol diacrylate (HDDA) or an HDDA derivative, and at least one derivative of polyethylene glycol (PEG) selected from the group consisting of: PEG-acrylate, PEG-diacrylate, and any multi-arm PEG-acrylate.

27 Claims, 28 Drawing Sheets
(23 of 28 Drawing Sheet(s) Filed in Color)

(51) Int. Cl.
| | | |
|---|---|---|
| B29C 64/135 | (2017.01) | |
| B33Y 70/00 | (2020.01) | |
| C12M 1/00 | (2006.01) | |
| C12M 1/12 | (2006.01) | |
| B29L 31/00 | (2006.01) | |
| B29K 83/00 | (2006.01) | |
| B29K 33/04 | (2006.01) | |
| B33Y 10/00 | (2015.01) | |

(52) U.S. Cl.
 CPC ............ *C12M 23/20* (2013.01); *C12M 25/02* (2013.01); *G01N 33/5058* (2013.01); *B29K 2033/04* (2013.01); *B29K 2083/00* (2013.01); *B29L 2031/7532* (2013.01); *B33Y 10/00* (2014.12); *C12N 2533/30* (2013.01); *C12N 2535/00* (2013.01); *C12N 2539/00* (2013.01)

(58) Field of Classification Search
 CPC .... B29C 64/135; B33Y 70/00; B29K 2083/00
 See application file for complete search history.

(56) References Cited

U.S. PATENT DOCUMENTS

| | | |
|---|---|---|
| 10,845,360 B2 | 11/2020 | Van Vliet et al. |
| 2004/0009593 A1 | 1/2004 | Keirstead et al. |
| 2007/0099294 A1 | 5/2007 | Yang et al. |
| 2014/0134729 A1 | 5/2014 | Shogbon et al. |
| 2016/0067375 A1 | 3/2016 | Holmes et al. |
| 2016/0089837 A1 | 3/2016 | Hsi et al. |
| 2016/0251646 A1 | 9/2016 | Guire et al. |
| 2017/0072105 A1 | 3/2017 | Jeffries et al. |
| 2017/0328888 A1 | 11/2017 | Van Vliet et al. |
| 2019/0242878 A1 | 8/2019 | Van Vliet et al. |

FOREIGN PATENT DOCUMENTS

| | | |
|---|---|---|
| CN | 106039417 A | 10/2016 |
| CN | 106215245 A | 12/2016 |
| CN | 106283216 A | 1/2017 |
| CN | 106492273 A | 3/2017 |
| GB | 2397824 A | 8/2004 |
| KR | 101622054 B1 | 5/2016 |
| WO | 2003070171 A3 | 8/2003 |
| WO | 2004094586 A2 | 11/2004 |
| WO | 2013074972 A1 | 5/2013 |
| WO | 2013172831 A1 | 11/2013 |
| WO | 2014100199 A1 | 6/2014 |
| WO | 2014116946 A1 | 7/2014 |
| WO | 2015048355 A1 | 4/2015 |
| WO | 2016077551 A1 | 5/2016 |
| WO | 2016168485 A1 | 10/2016 |
| WO | 2016192733 A1 | 12/2016 |
| WO | 2016196774 A1 | 12/2016 |
| WO | 2017017003 A1 | 2/2017 |
| WO | 2017147501 A1 | 8/2017 |
| WO | WO 2017/147501 A1 | 8/2017 |
| WO | WO 2018/208909 A1 | 11/2018 |

OTHER PUBLICATIONS

Kim et al. Characterization of the crosslinking kinetics of multi-arm poly(ethylene glycol) hydrogels formed via Michael-type addition. Soft Matter (2016), 12, 2076-2085. (Year: 2016).*
Sun et al. Novel Compound-Forming Technology Using Bioprinting and Electrospinning for Patterning a 3D Scaffold Construct with Multiscale Channels. Micromachines (Dec. 2016), 7, 238, 14 pages. (Year: 2016).*
Wei et al. Fabrication of PLGA nanofibers on PDMS micropillars for neuron culture studies. Microelectronic Engineering (Jan. 2017), 175, 67-72. (Year: 2017).*
Meng et al. Electrospun crosslinked poly(acrylic acid) fiber constructs: towards a synthetic model of the cortical layer of nerve. Polym. Int. (2015), 64, 42-48. (Year: 2015).*
Hobzova, R. et al., "Embedding of Bacterial Cellulose Nanofibers within PHEMA Hydrogel Matrices: Tunable Stiffness Composites with Potential for Biomedical Applications," Journal of Nanomaterials, vol. 2018, Article ID 5217095, 11 pages (2018).
Rosser, JM et al., "Recent Advances Of Biologically Inspired 3D Microfluidic Hydrogel Cell Culture Systems," Journal of Cell Biology & Cell Metabolism, ISSN: 2381-1943, 34 pages, (May 2015).
Zeiger, A., "Chemomechanics at Cell-Cell and Cell-Matrix Interfaces Critical to Angiogenesis," Department of Materials Science and Engineering, Massachusetts Institute of Technology (2013).
Zheng, X et al., "Ultralight, Ultrastiff Mechanical Metamaterials," Science, 344(6190): 1373-1377 (2014).
Huang, J. et al., "Electrical regulation of Schwann cells using conductive polypyrrole/chitosan polymers," J Biomed Mater. Res. Part A 93(1): 164-74 (2010).
Espinosa-Hoyos et al., Published online Jan. 11, 2018, Engineered 3D-printed artificial axons, Scientific Reports 8:478 I DOI: 10.1038/S41598-017-18744-6, 13 pages (2018).
Jagielska, A. et al., "Mechanical strain promotes oligodendrocyte differentiation by global changes of gene expression," Front. Cell. Neurosci. 11, 93 (2017).
Howe, C. L. "Coated Glass and Vicryl Microfibers as Artificial Axons," Cells Tissues Organs 183, 180-194 (2006).
Non-Final Office Action for U.S. Appl. No. 15/442,530, titled: Neuronal Axon Mimetics for In Vitro Analysis of Neurological Diseases, Myelination, and Drug Screening, dated Dec. 17, 2018.
Non-Final Office Action for U.S. Appl. No. 16/387,323, entitled: "Neuronal Axon Mimetics For In Vitro Analysis Of Neurological Diseases, Myelination, And Drug Screening", dated Dec. 23, 2019.
Espinosa-Hoyos et al., "Engineered 3D-printed artificial axons", Jan. 11, 2018, Scientific Reports 8:478 I DOI: 10.1038/s41598-017-18744-6, 13 pages (Year: 2018).
PCT International Preliminary Report on Patentability dated Nov. 12, 2019 for International Application No. PCT/US2018/031792; Entitled "Engineered 3D-Printed Artificial Axons"; consisting of 8 pages.
International Preliminary Report on Patentability dated Aug. 28, 2018 for International Application No. PCT/US2017/019463, entitled "Neuronal Axon Mimetics For In Vitro Analysis Of Neurological Diseases, Myelination, And Drug Screening."
Liu, C. et al., "Novel electrospun polylactic acid nanocomposite fiber mats with hybrid graphene oxide and nanohydroxyapatite reinforcements having enhanced biocompatibility," Polymers (Basel), 8: 287-306 (2016).
Liu, Y. et al., "3D bio-nanofibrous PPy/SIBS mats as platforms for cell culturing," Chemical Communications, 32: 3729-3731 (2008).
Lourenço, T. et al., "Modulation of Oligodendrocyte Differentiation by Mechanotransduction," Front Cell Neurosci., 10: 277 (2016).
Lu, Y. et al., "A digital micro-mirror device-based system for the microfabrication of complex, spatially patterned tissue engineering scaffolds," J. Biomed. Mater. Res. Part A, 77A: 396-405 (2006).
Lu, Y. et al., "Viscoelastic properties of individual glial cells and neurons in the CNS," Proc. Natl. Acad. Sci., 103(47): 17759-17764 (2006).
Malda, J. et al. "25th anniversary article: engineering hydrogels for biofabrication," Adv. Mater., 25(36): 5011-5028 (2013).
Martin, R. et al., "Electrospinning 3D scaffolds for use in neural tissue engineering," Materials Research Society Symposium Proceedings, 1798: 13-18 (2015).
Mccarthy, K. et al., "Preparation of separate astroglial and oligodendroglial cell cultures from rat cerebral tissue," J. Cell Biol., 85: 890-902 (1980).
Mei, F. et al., "Micropillar arrays as a high-throughput screening platform for therapeutics in multiple sclerosis," Nat. Med., 20, 954-960 (2014).
Merolli, A., et al., "The use of a suspended carbon fiber culture to model myelination by human Schwann cells," J Mater Sci: Mater Med., 28:57 (2017).

(56) References Cited

OTHER PUBLICATIONS

Miller, K. et al., "Mechanical properties of brain tissue in-vivo: experiment and computer simulation," J. Biomech., 33: 1369-1376 (2000).
Moeendarbary, E. et al., "The soft mechanical signature of glial scars in the central nervous system," Nat. Commun., 8 (14787) (2017).
Murphy, M. et al., "Decreased brain stiffness in Alzheimer's disease determined by magnetic resonance elastography," J. Magn. Reson. Imaging 34: 494-498 (2011).
Murphy, M. et al., "Regional brain stiffness changes across the Alzheimer's disease spectrum," NeuroImage. Clin., 10: 283-290 (2016).
Ortega, I. et al., "Fabrication of biodegradable synthetic perfusable vascular networks via a combination of electrospinning and robocasting," Biomater. Sci., 3: 592-596 (2015).
Othon, C. et al., "Single-cell printing to form three-dimensional lines of olfactory ensheathing cells," Biomed. Mater. 3 (3) (2008).
Pai, C., "Morphology and mechanical properties of electrospun polymeric fibers and their nonwoven fabrics," Massachusetts Institute of Technology, Dept. of Chemical Engineering (2011).
Palchesko, R. et al., "Development of Polydimethylsiloxane substrates with turnable elastic modulus to study cell mechanobiology in muscle and nerve," PLoS ONE, 7(12): 1-13 (2012).
Pan, Y., "Study of separation force in constrained surface projection stereolithography," Rapid Prototyp. J., 23(2): 353-361 (2017).
Pang, Y. et al., "Neuron-oligodendrocyte myelination co-culture derived from embryonic rat spinal cord and cerebral cortex," Brain Behavior, 2: 53-67 (2012).
Raredon, M., "Design and fabrication of physiologic tissue scaffolds using projection-micro-stereolithography," Massachusetts Institute of Technology, Dept. of Materials Science and Engineering (2014).
Riek, K. et al., "Magnetic resonance elastography reveals altered brain viscoelasticity in experimental autoimmune encephalomyelitis," NeuroImage Clin. 1: 81-90 (2012).
Rosenberg, S. et al., "The geometric and spatial constraints of the microenvironment induce oligodendrocyte differentiation," Proc. Natl. Acad. Sci., 105(38): 14662-14667 (2008).
Roussos, P. et al., "Schizophrenia: susceptibility genes and oligodendroglial and myelin related abnormalities," Front. Cell. Neurosci. 8(5) (2014).
Schmidt, C. et al., "Stimulation of neurite outgrowth using an electrically conducting polymer," Proceedings of the National Academy of Sciences of the USA, Applied Biological Sciences, 94: 8948-8953 (1997).
Schregel, K. et al., "Demyelination reduces brain parenchymal stiffness quantified in vivo by magnetic resonance elastography," Proc. Natl. Acad. Sci., 109: 6650-6655 (2012).
Shah, S. et al., "Guiding stem cell differentiation into oligodendrocytes using graphene-nanofiber hybrid scaffolds," Adv. Mater., 26: 3673-3680 (2014).
Shi, G. et al., "Electrical stimulation enhances viability of human cutaneous fibroblasts on conductive biodegradable substrates," J Biomed. Mater Res. Part A, 84A: 1026 (2007).
Shim, J. et al., "Development of a hybrid scaffold with synthetic biomaterials and hydrogel using solid freeform fabrication technology," Biofabrication, 3, 034102: 1-9 (2011).
Shimizu, T. et al., "YAP functions as a mechanotransducer in oligodendrocyte morphogenesis and maturation," Glia, 65: 360-374 (2017).
Silva, E. et al., "Size Effects on the Stiffness of Silica Nanowires," Small, 2: 239-243 (2006).
Singh, V. et al., "Scalable Fabrication of Low Elastic Modulus Polymeric Nanocarriers With Controlled Shapes for Diagnostics and Drug Delivery," J. Micro Nano-Manufacturing, 3, 011002 (2015).
Smoukov, S. et al., "Scalable Liquid Shear-Driven Fabrication of Polymer Nanofibers," Advanced Materials, 27(16): 2642-2647 (2015).
Sobel, R. et al., "Fibronectin in multiple sclerosis lesions," Am. J. Pathol., 135(1): 161-168 (1989).
Stoffels, J. et al., "Fibronectin aggregation in multiple sclerosis lesions impairs remyelination," Brain, 136: 116-131 (2013).
Streitberger, K. et al., "Brain viscoelasticity alteration in chronic-progressive multiple sclerosis," PLoS One, 7(1): e29888 (2012).
Sun, C. et al., "Projection micro-stereolithography using digital micro-mirror dynamic mask," Sensors and Actuators A, 121: 113-120 (2005).
Sun, L. et al., "Direct-Write Assembly of 3D Silk/Hydroxyapatite Scaffolds for Bone Co-Cultures," Advanced Healthcare Materials, 1(6): 729-735 (2012).
Sur, S. et al., "Tuning supramolecular mechanics to guide neuron development," Biomaterials, 34(20): 4749-4757 (2013).
Tkachev, D. et al., "Oligodendrocyte dysfunction in schizophrenia and bipolar disorder," Lancet, 362: 798-805 (2003).
Tuck, S., "Critical variables in the alignment of electrospun PLLA nanofibers," Materials Science & Engineering C, Biomimetic and Supramolecular Systems, 32(7): 1779-84 (2012).
Tumbleston, J. et al., "Continuous liquid interface production of 3D objects," Science, 347(6228): 1349-1352 (2015).
Urbanski, M. et al., "Myelinating glia differentiation is regulated by extracellular matrix elasticity," Scientific Reports, 6: 33751 (2016).
Valentini, R. et al., "Electrically charged polymeric substrates enhance nerve fibre outgrowth in vitro," Biomaterials 13 (3):183-190 (1992).
Wu, Y. et al., "Alterations of myelin morphology and oligodendrocyte development in early stage of Alzheimer's disease mouse model," Neuroscience Letters, 642:102-106 (2017).
Xanofi, Inc. http://xanofi.com/news/worlds-first-3d-polymer-nanofiber-scaffolding-printer/.
Xia, C. et al., "Solvent-driven polymeric micro beam device," J. Micromechanics Microengineering, 20(8) (2010).
Xu, W. et al., "Organic core-sheath nanowire artificial synapses with femtojoule energy consumption," Science Advances, 2(6): e1501326 (2016).
Yu, L. et al., "Promoting neuron adhesion and growth," MaterialsToday, 11(5): 36-43 (2008).
Aoun, L. et al., "Microdevice arrays of high aspect ratio Poly(DiMethylSiloxane) pillars for the investigation of multicellular tumour spheroid mechanical properties," Lab Chip 14(13): 2344-2353 (2014).
Arulmoli, J. et al., "Static stretch affects neural stem cell differentiation in an extracellular matrix-dependent manner," Sci. Rep. 5: 8499 1-8 (2015).
Baker, B. et al., "Cell-mediated fiber recruitment drives extracellular matrix mechanosensing in engineered fibrillar microenvironments," Nat. Mater. 14(12): 1262-1268 (2015).
Baker, S. et al., "Determining the mechanical properties of electrospun poly-E-caprolactone (PCL) nanofibers using AFM and a novel fiber anchoring technique," Mater. Sci. Eng. C 59: 203-212 (2016).
Barry, R. et al., "Direct-Write Assembly of 3D Hydrogel Scaffolds for Guided Cell Growth," Adv. Mater., 21(23): 2407-2410 (2009).
Bechler, M. et al., "CNS Myelin Sheath Lengths are an Intrinsic Property of Oligodendrocytes," Curr. Biol. 25: 2411-2416 (2015).
Bradel, E. et al., "Cultured neonatal rat oligodendrocytes elaborate myelin membrane in the absence of neurons," J. Neurosci. Res. 9: 381-392 (1983).
Bullock, P. et al., "Glass micro-fibers: a model system for study of early events in myelination," J. Neurosci. Res. 27: 383-393 (1990).
Chandra, D., "Capillary Force in High Aspect-Ratio Micropillar Arrays," University of Pennsylvania, ProQuest Dissertations Publishing (2009).
Chong, S. et al., "Neurite outgrowth inhibitor Nogo-A establishes spatial segregation and extent of oligodendrocyte myelination," Proc. Natl. Acad. Sci. 109(4): 1299-1304 (2012).
Christ, A. et al., "Mechanical difference between white and gray matter in the rat cerebellum measured by scanning force microscopy," J. Biomech. 43(15): 2986-2992 (2010).
Dinis, T. et al., "3D multi-channel bi-functionalized silk electrospun conduits for peripheral nerve regeneration," Journal of the Mechanical Behavior of Biomedical Materials, 41: 43-55 (2015).
Espinosa-Hoyos, D. et al., "Poly(HDDA)-Based Polymers for Microfabrication and Mechanobiology," Biomaterials and Soft Materials 2(24): 1315-1321 (2017).

(56) References Cited

OTHER PUBLICATIONS

Franklin, R., "Why does remyelination fail in multiple sclerosis?," Nat. Rev. Neurosci. 3: 705-714 (2002).
Franze, K. et al., "Mechanics in neuronal development and repair," Annu. Rev. Biomed. Eng. 15: 227-251 (2013).
Friese, M. et al., "Acid-sensing ion channel-1 contributes to axonal degeneration in autoimmune inflammation of the central nervous system," Nat. Med. 13: 1483-1489 (2007).
Gardner, A. et al., "Myelination of rodent hippocampal neurons in culture," Nat. Protoc. 7(10): 1774-1782 (2012).
Ghasemi-Mobarakeh L. et al., "Electrical stimulation of nerve cells using conductive nanofibrous scaffolds for nerve tissue engineering," Tissue Engineering Part A, 15(11): 3605-3619 (2009).
Gratson, G. et al., "Microperiodic structures: Direct writing of three-dimensional webs," Nature 428: 386 (2004).
Hanson-Shepherd, J. et al., "3D Microperiodic Hydrogel Scaffolds for Robust Neuronal Cultures," Adv. Funct. Mater., 21(1): 47-54 (2011).
Hardin, J. et al., "Microfluidic printheads for multimaterial 3D printing of viscoelastic inks," Adv. Mater. 27: 3279-3284 (2015).
Harlow, D. et al., "Inhibitors of myelination: ECM changes, CSPGs and PTPs," Exp. Neurol. 251: 39-46 (2014).
Hernandez, M. et al., "Mechanostimulation promotes nuclear and epigenetic changes in oligodendrocytes," J. Neurosci. 36(3): 806-813 (2016).
Hildebrand, C. et al., "Myelinated nerve fibres in the CNS," Prog. Neurobiol. 40: 319-384 (1993).
Homan, K. et al., "3D Printing of Hydrogel Scaffolds with Tailored Composition and Stiffness," Harvard School of Engineering, Wyss Institute (2014).
Hutter, J. et al., "Calibration of atomic-force microscope tips," Rev. Sci. Instrum. 64(7): 1868-1873 (1993).
International Search Report and Written Opinion dated Jun. 12, 2017 for International Application No. PCT/US2017/019463, entitled "Neuronal Axon Mimetics For In Vitro Analysis Of Neurological Diseases, Myelination, And Drug Screening."
International Search Report and Written Opinion dated Aug. 22, 2018 for International Application No. PCT/US2018/031792, entitled "Cell-Mimetic Device".
Jagielska, A. et al., "Extracellular Acidic pH Inhibits Oligodendrocyte Precursor Viability, Migration, and Differentiation," PLoS ONE, 8(9): 1-13 (2013).
Jagielska, A. et al., "Mechanical Environment Modulates Biological Properties of Oligodendrocyte Progenitor Cells," Stem Cells & Dev., 21(16): 2905-2914 (2012).
Jarjour, A. et al., "In vitro modeling of central nervous system myelination and remyelination," Glia 60(1): 1-12 (2012).
Jeong, S. et al., "Development of electroactive and elastic nanofibers that contain polyaniline and poly(L-lactide-co-epsilon-caprolactone) for the control of cell adhesion," Macromol Biosci 8: 627-637 (2008).
Kador, K. et al., "Control of Retinal Ganglion Cell Positioning and Neurite Growth: Combining 3D Printing with Radial Electrospun Scaffolds," Tissue Engineering—Part A, 22(3-40): 286-294 (2016).
Kerman, B. et al., "In vitro myelin formation using embryonic stem cells," Development, 142: 2213-2225 (2015).
Kippert, A. et al., "Actomyosin contractility controls cell surface area of oligodendrocytes," BMC Cell Biology 10:71 (2009).
Kohlschütter, A. et al., "Childhood leukodystrophies: A clinical perspective," Expert Review of Neurotherapeutics, 11 (10): 1485-1496 (2011).
Kolesky, D. et al., "3D Bioprinting of Vascularized, Heterogeneous Cell-Laden Tissue Constructs," Adv. Mater., vol. 26, Issue 19, 3124-3130 (2014).
Kolesky, D. et al., "Three-dimensional bioprinting of thick vascularized tissues," Proceedings of the National Academy of Sciences, 113(12): 3179-3184 (2016).
Kotwal, A. et al., "Electrical stimulation alters protein adsorption and nerve cell interactions with electrically conducting biomaterials," Biomaterials 22: 1055-1064 (2001).
Lakhani, B. et al., "Hemispheric asymmetry in myelin after stroke is related to motor impairment and function," NeuroImage Clinic, 14: 344-353 (2017).
Lariosa-Willingham, K. et al., "Development of a central nervous system axonal myelination assay for high throughput screening," BMC Neuroscience, 17: 16 (2016).
Lee, H. et al., "Direct alignment and patterning of silver nanowires by electrohydrodynamic jet printing," Small 10: 3918-3922 (2014).
Lee, M. et al., "Development of a 3D printer using scanning projection stereolithography," Scientific Reports, 5: 9875 (2015).
Lee, S. et al., "A culture system to study oligodendrocyte myelination processes using engineered nanofibers," Nature Methods, 9(9): 917-922 (2012).
Lee, S. et al., "A rapid and reproducible assay for modeling myelination by oligodendrocytes using engineered nanofibers," Nat. Protoc. 8, 771-782 (2013).
Lee, S. et al., "Fabrication of a Highly Aligned Neural Scaffold via a Table Top Stereolithography 3D Printing and Electrospinning," Tissue Engineering Part A, 23(11-12): 491-502 (2017).
Levental, I. et al., "Soft biological materials and their impact on cell function," Soft Matter, 3: 299-306 (2007).
Li, M. et al., "Electrospinning polyaniline-contained gelatin nanofibers for tissue engineering applications," Biomaterials, 27: 2705-2715 (2006).
Li, Y. et al., "Nanofibers support oligodendrocyte precursor cell growth and function as a neuron-free model for myelination study," Biomacromolecules, 15(1): 319-326 (2014).
Liewald, D. et al., "Distribution of axon diameters in cortical white matter: an electron-microscopic study on three human brains and a macaque," Biological Cybernetics, 108(5): 541-557 (2014).

\* cited by examiner

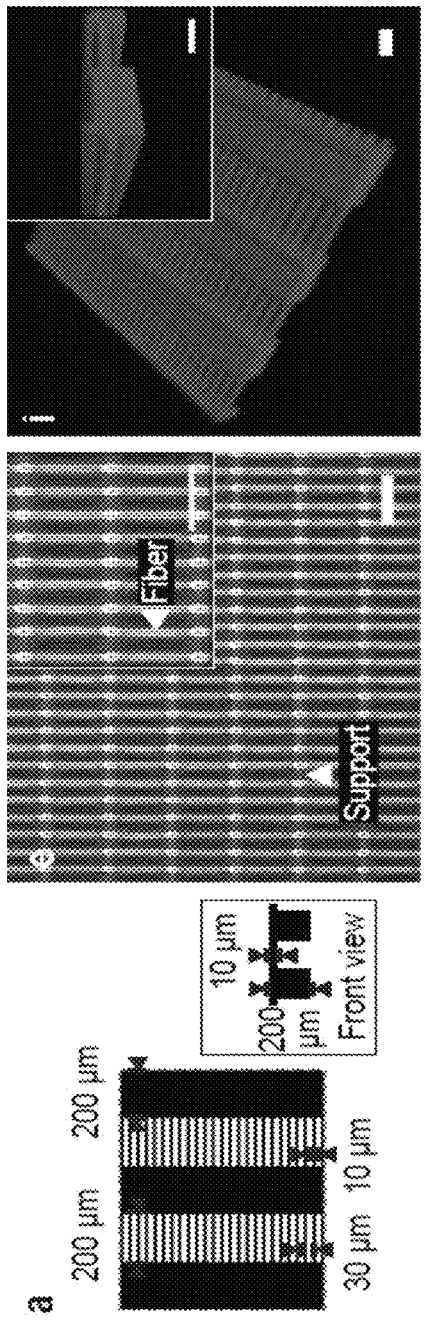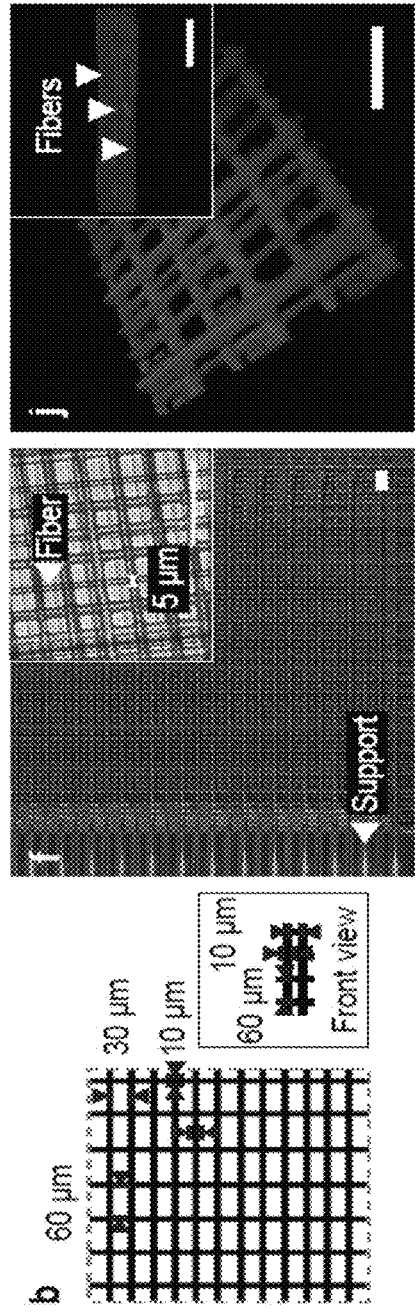
FIG. 4A  FIG. 4E  FIG. 4I
FIG. 4B  FIG. 4F  FIG. 4J

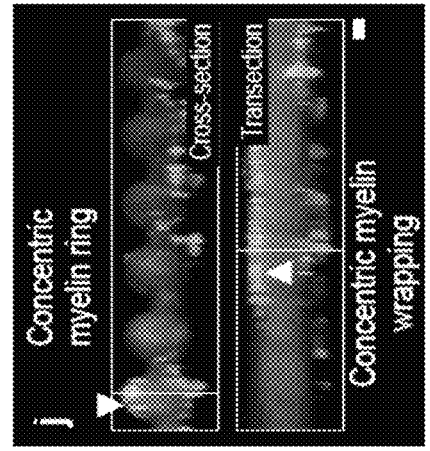
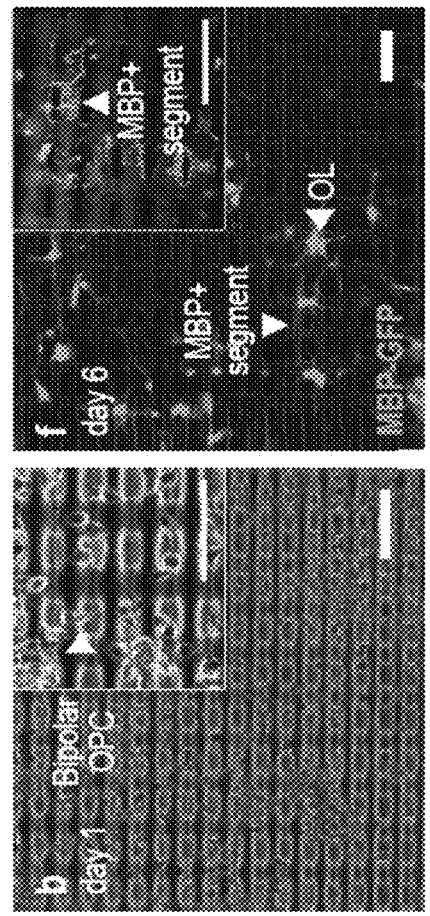
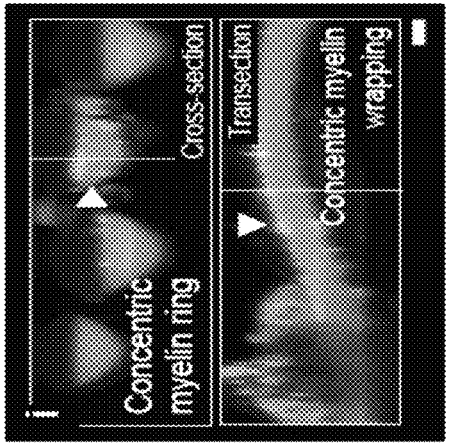
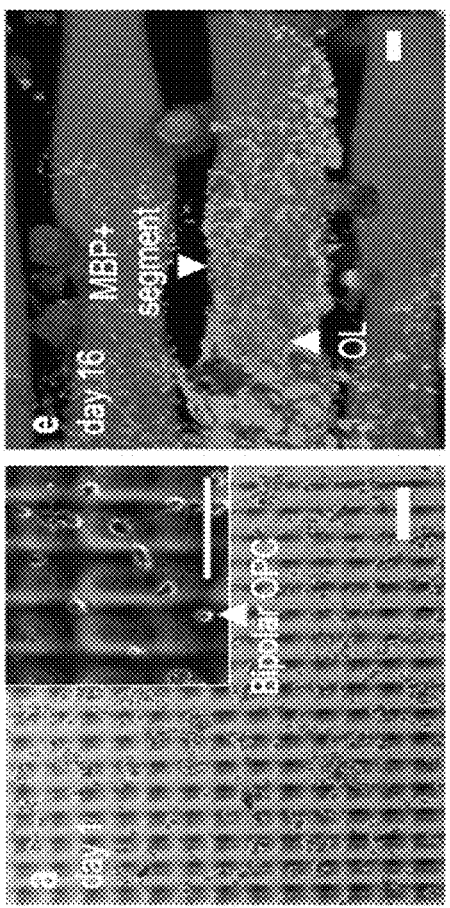
FIG. 5A  FIG. 5B  FIG. 5E  FIG. 5F  FIG. 5I  FIG. 5J

| Component | Ink 0 (wt%) | Ink 1 (wt%) | Ink 2 (wt%) |
|---|---|---|---|
| pHEMA (1 MDa) | 10 | 10 | 10 |
| pHEMA (300 kDa) | 25 | 25 | 25 |
| HEMA monomer | 40 | 5 | 10 |
| Water | 23.7 | 33.7 | 33.7 |
| Ethanol | 0 | 25 | 20 |
| EGDMA (comonomer) | 1 | 1 | 1 |
| Irgacure (initiator) | 0.3 | 0.3 | 0.3 |

ENGINEERED 3D-PRINTED ARTIFICIAL AXONS

RELATED APPLICATION

This application claims the benefit of U.S. Provisional Application No. 62/504,476, filed on May 10, 2017. The entire teachings of the above application are incorporated herein by reference.

BACKGROUND

Currently available devices for the study of neurological diseases and neural cell interactions include two-dimensional (2D) stiff polystyrene tissue culture dishes, mixed neuronal-glial cell cultures, and organotypic culture using tissue slices. The first format, 2D polystyrene tissue culture dishes, oversimplifies an in vivo environment because it provides flat and stiff surfaces upon which cell cultures are grown, which are very different from three-dimensional (3D), topographically complex, and mechanically compliant neural tissue. The latter two formats are more similar to in vivo environments; however, there is inherent variability among neuronal cultures and tissue slices. Such cultures do not allow for systematic isolation of individual physical and chemical cues, which is necessary to understand underlying mechanisms. There is a strong need for devices that can provide an environment sufficiently similar to real neurons and neural tissue, while at the same time capable of delivering high reproducibility and reductionist structure. Such devices are critical to accelerate development of therapies for many currently incurable neurological diseases.

SUMMARY

Methods and devices of the present invention provide for improved neuronal axon mimics, including mimics having diameters below 10 micrometers and tunable elastic moduli within the megaPascal to Pascal range. Devices and methods of the present invention can advantageously provide for cell-mimetic devices having features or conditions (e.g. geometry, stiffness) more similar to biological neurons than existing devices.

A cell-mimetic device includes an array of fibers comprised of a material containing hexanediol diacrylate (HDDA), or an HDDA derivative, and at least one derivative of polyethylene glycol (PEG) derivative, selected from the group consisting of: PEG-acrylate, PEG-diacrylate, and any multi-arm PEG-acrylate.

For example, the material can comprise poly(HDDA-co-starPEG). The poly(HDDA-co-starPEG) material can comprise about 1% to about 99% w/w HDDA, for example, about 5% to about 50% w/w HDDA, or about 5% to about 35% w/w HHDA, or about 10% to 30% w/w HDDA.

Cell-mimetic devices, for example, comprising poly(HDDA-co-starPEG), can have fibers with a stiffness of between about 0.1 kPa and 200 kPa, 0.1 kPa and 50 kPa, 0.1 kPa and 10 kPa, or about 0.1 kPa and 1 kPa. At least a subset of the fibers can be arranged in either a horizontal configuration or a vertical pillar configuration. Horizontally-arranged fibers can include suspended portions (not contacting the substrate). For example, at least a subset of fibers can be suspended between supports at a distance of about 10 µm to about 500 µm or of about 100 µm to about 200 µm. Vertically-arranged fibers can include free-standing pillars. For example pillars can have height of about 10 µm to about 200 µm, or about 10 µm to about 150 µm, or about 10 µm to about 100 µm, or about 20 µm to about 100 µm, or about 30 µm to about 100 µm, or about 30 µm to about 80 µm. The fibers can also be modified by a surface ligand. The array of fibers can be arranged in a three-dimensional (3D) structure representing a model of neuronal axons. Fibers can have a diameter of about 0.1 µm to about 20 µm, for example, of about 1 µm to about 10 µm, of about 1 µm to about 5 µm, of about 0.1 µm to about 5 µm, or of about 0.1 µm to about 2 µm.

An assay method includes contacting a cell-mimetic device with at least one population of cells and studying at least one feature of an interaction of the at least one population of cells with at least one of: (a) the device, (b) a drug or active pharmaceutical ingredient, and (c) another population of cells.

Manufacturing of a cell mimetic device can include Projection Microstereolithography (PµSL) methods. For example, the method can include generating a digital image of a microstereolithography mask and projecting the image, illuminated by a light source, onto a resin bath comprising a material comprising hexanediol diacrylate (HDDA) or an HDDA derivative and at least one derivative of polyethylene glycol (PEG) selected from the group consisting of PEG-acrylate, PEG-diacrylate, and any multi-arm PEG-acrylate. The method further includes exposing the resin bath to the light source causing an exposed portion of the material to cure.

The method can further include generating a series of digital images, sequentially projecting the series of digital images onto the resin bath, and sequentially translating the resin bath to cure layers of the material within the resin bath. Generating a series of digital images can include generating cross-sectional images of a three-dimensional (3D) modeled fiber array structure. The 3D modeled structure can include a fiber array of either a horizontal or a vertical configuration of fibers, or a tilted configuration of fibers, for example, fibers positioned at an angle between 0° and 90° with respect to a supporting layer of the array, for example, between about 10° and about 80° or between about 30° and about 60°. A cured portion of the material can include a three-dimensional structure comprising a fiber array.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 4A is a schematic of an example of PDMS fibers for direct ink printing.

FIG. 4B is a schematic of an example of pHEMA fibers for direct ink printing.

FIG. 4E is a phase contrast microscope image of a fabricated sample of the PDMS fibers of FIG. 4A.

FIG. 4F is a phase contrast microscope image of a fabricated sample of the pHEMA fibers of FIG. 4B.

FIG. 4I is a confocal microscopy image of the fibers of FIG. 4E. Scale bars are 100 μm.

FIG. 4J is a confocal microscopy image of the fibers of FIG. 4F. Scale bars are 100 μm.

FIG. 5A is an image of Oligodendrocyte Precursor Cells (OPC) engagement, migration, and proliferation at day 1 after seeding on artificial axons fabricated with PDMS by direct ink printing. Scale bars are 100 μm.

FIG. 5B is an image of OPC engagement, migration, and proliferation at day 1 after seeding on artificial axons fabricated with pHEMA by direct ink printing. Scale bars are 100 μm.

FIG. 5E is a plane view of oligodendrocyte differentiation and myelin wrapping on the artificial axons of FIG. 5A.

FIG. 5F is a plane view of oligodendrocyte differentiation and myelin wrapping on the artificial axons of FIG. 5B.

FIG. 5I is an image of cross- and trans-views of Myelin Basic Protein (MBP) positive myelin membrane around the artificial axons of FIG. 5A. Scale bars are 10 μm.

FIG. 5J is an image of cross- and trans-views of MBP positive myelin membrane around on the artificial axons of FIG. 5B. Scale bars are 10 μm.

DETAILED DESCRIPTION

Figure 1A:
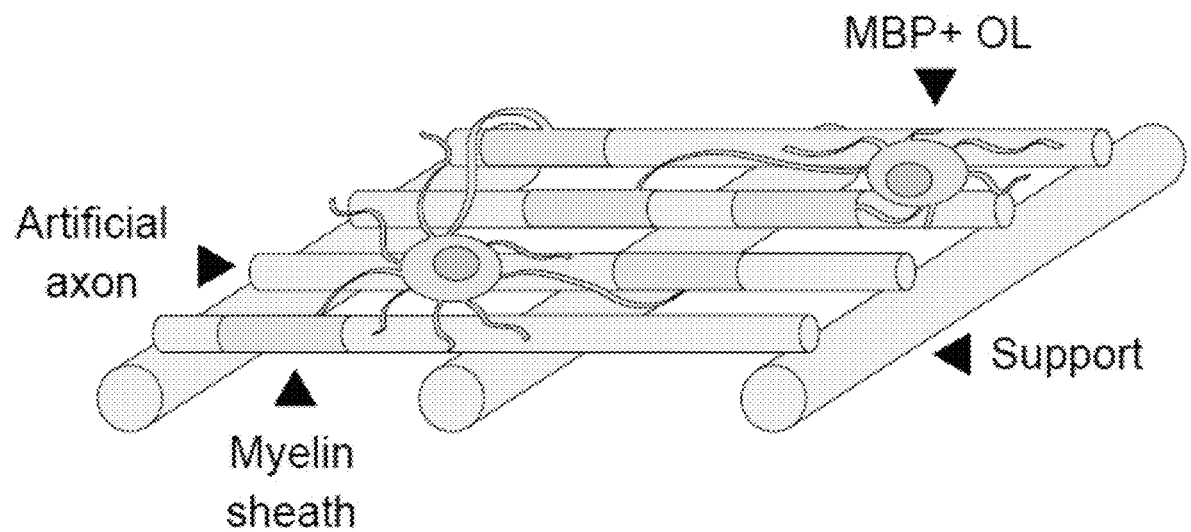
FIG. 1A is a schematic illustrating an example of artificial axons in a horizontal configuration including suspended fibers. Myelin, being wrapped around axon fibers by oligodendrocytes, is shown in green.

A description of example embodiments follows.

As further described in the recent scientific publication by co-inventors, D. Espinosa-Hoyos et al, published on Dec. 16, 2017[1], the entire contents of which are incorporated herein by reference, myelination is a process by which glial cells, such as oligodendrocytes, produce and wrap a protective, insulating membrane sheet around neuronal axons, which are generally cylindrical in shape. This process can be referred to as ensheathing and is a key developmental milestone in vertebrate neuronal function. Compromised myelin sheath formation and/or repair are hallmarks of several central nervous system diseases [2, 3, 4]. Thus, in vitro models and materials to understand and promote the interaction between glial cells and neurons are of both scientific and technological interest.

Engineering of systems for the modeling of myelination can provide a necessary balance between the geometrical complexity of three-dimensional (3D) in vivo tissue microenvironments and the simplicity of currently available in vitro models, which often feature transparent, flat, and/or stiff materials that are optimized for cell culture and imaging applications but do not provide physical mimicry of the neuronal environment. Tissue slice cultures are often less than ideal for the study of healthy and dysfunctional myelination because biological variations within tissue slice cultures often obfuscate elucidation of mechanisms and causality [5]. However, tissue slice cultures can reflect many physical, biochemical, and mechanical cues that are anticipated in vivo. In contrast, isolated oligodendrocyte populations can produce myelin-resembling membranes at the extensions of their processes, which can be easily imaged on glass and polystyrene surfaces. However, isolated oligodendrocyte populations grown on, for example, cell culture plates, neglect the physical and biochemical features of contact and encircling between oligodendrocytes and fiber-like axons of neurons.

The co-culture of neurons and glial cells on engineered materials is a reductionist compromise that has been used extensively in simplified myelination assays and has recently been optimized for high-throughput drug screening [6]. However, inclusion and interaction of both cell types also confers other challenges in interpretation and image-based quantification. For example, co-culturing generally involves a significant increase in time and cost over other methods, while resulting in reduced reproducibility. Co-culturing also includes the potential for off-target and cell-type cross-talk that can complicate interpretation of mechanisms for the cell type of interest. Thus, while neuronal-glia co-cultures remain powerful tools for validation, more minimally permissive approaches that provide sufficient fidelity of glial-axon interactions are needed to enable basic mechanistic studies and facilitate the discovery of therapeutics.

Mimicking key features of neuronal axon fibers has been explored by others. For example, Bullock et al. [7] and Howe [8] cultured oligodendrocytes in close proximity to glass microfibers in the absence of neurons and observed occasional loose monolayer wrapping of myelin membranes. Rosenberg et al. [9] showed that intact, fixed axons enabled compact, concentric, and multilaminar myelination, suggesting that dynamic axonal signaling is not required to initiate or complete ensheathment. Lee et al. [10] and Bechler et al. [11] used electrospun fibers to decouple molecular cues from biophysical properties, such as axon diameter. They observed preferential myelin wrapping around larger diameter fibers. Mei et al. developed fused silica cones, which could be viewed in-plane for high-throughput imaging and screening of drug effects on oligodendrocyte production or wrapping [12, 13]. While providing the potential for rapid comparative analysis of various conditions on myelin production, the patterned structures of Mei [13] were conical, not cylindrical, as are biological axons, and did not elicit the concentric, multilayered membrane compaction that is considered to be a key feature of myelination. Moreover, such materials as described in the references herein (e.g., materials ranging from heavily crosslinked polymers to glass, to which cells are chemically fixed), all exhibited mechanical stiffness that was at least an order of magnitude greater than that of biological axons. Even two-dimensional (2D) co-culturing methods involve oligodendroglia adhering to stuff substratum typically composed of polystyrene or glass.

Indeed, a key axonal characteristic that is neglected in other reductionist myelination models is the mechanical stiffness of neuronal axons and brain tissue. Nervous tissue is among the most compliant of biological "soft tissues," with a Young's elastic modulus of about 0.1 kPa to about 1 kPa [14, 15, 16], which is six orders of magnitude lower in stiffness than silica glass and tissue culture plastic. Additionally, glial cell lineages are mechanosensitive in vitro, with mechanical cues, such as stiffness of the material to which the cells adhere, modulating proliferation, migration, and differentiation of oligodendrocyte progenitor cells to myelinating oligodendrocytes [17]. Local reduction in tissue stiffness is reported in neurodegenerative disorders, such as Alzheimer's and multiple sclerosis, characterized by inflammation and decrease in myelin matter [18, 19].

Embodiments of the present invention include materials and methods for making cell mimetics (alternatively referred to as cell mimics) that can replicate biological axonal features in healthy and diseased contexts. Methods of the present invention can provide independent control of fiber geometry, mechanical stiffness, and surface ligand type. Cell-mimetic devices of the present invention can also enable direct imaging of glial cell interactions, including adhesion, migration, and full wrapping of axon fibers. As such, embodiments of the present invention provide for improved systems and methods by which future studies of myelination, cell interactions, and drug responses in a microenvironment can occur.

Additive manufacturing methods, polymers, and architectures are described that can provide for engineered microenvironments having varying degrees of complexity. With engineered microenvironments, for example, as shown in FIGS. 4A-7G and described herein, primary murine oligodendrocytes and human oligodendrocytes can fully wrap around cell-mimetic fibers, which exhibit axon-level stiffness, diameter, and spacing. Embodiments of the present invention can enable the study of myelination that is fiber-property dependent. Methods and devices of the present invention also provide for reproducibility and scalability, and can be adapted to exhibit features of distinct disease microenvironments, such as ligand-type functionalization, stiffness, and/or axonal diameter heterogeneity. For example, microenvironments can be adapted to replicate demyelination lesions, glial scars, and swollen axons.

Cell-Mimetic Designs

The invention relates, in some embodiments, to the provision of cell-mimetic devices. As used herein, a "cell-mimetic" is a structure that mimics one or more relevant features of a cell or a portion thereof. In some embodiments the cell mimetic is an "axon-mimetic," mimicking features of a neuronal axons (e.g., axons of peripheral neurons, or axons of central nervous system (CNS) neurons, such as from brain or spinal cord).

Figure 1B:
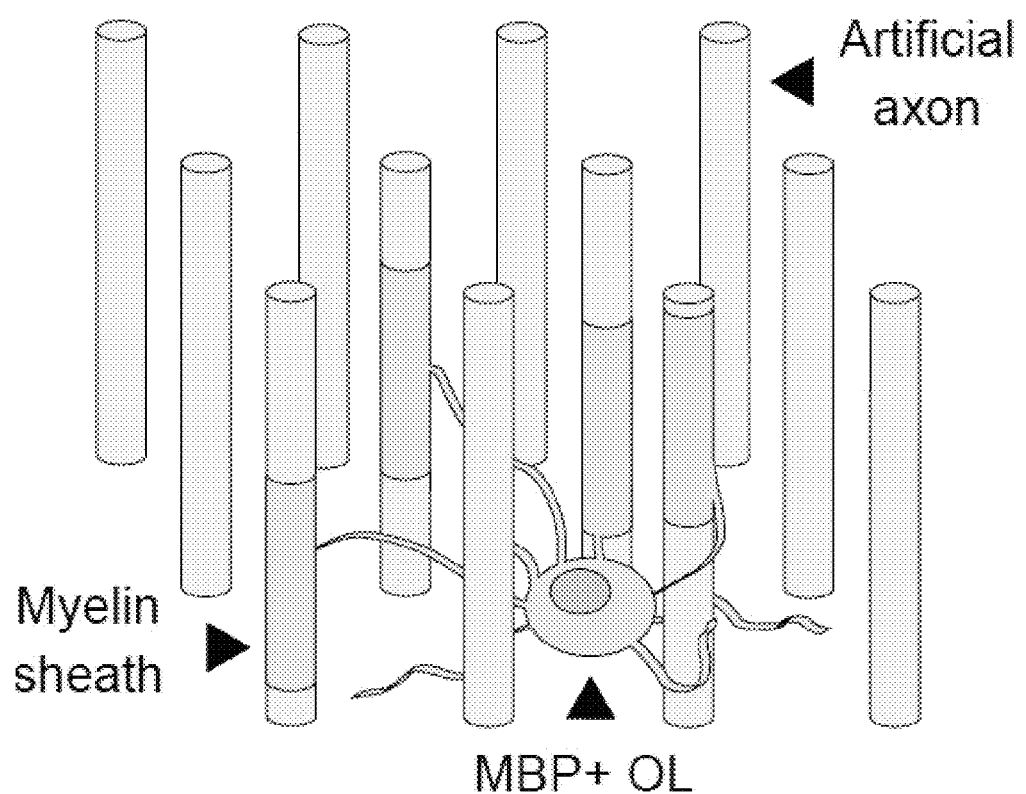
FIG. 1B is a schematic illustrating an example of artificial axons in a vertical configuration including freestanding fibers (e.g., pillars). Myelin, being wrapped around axon fibers by oligodendrocytes, is shown in green.

Cell-mimetic devices can include artificial axons, or arrays of artificial axons, having morphological and macroscopic features of axon tracts in the central nervous system (CNS), as shown in FIGS. 1A-1B. Relevant features of cells that can be mimicked by cell-mimetics include, without limitation: physical, mechanical, and biochemical properties, and gradients of any of these properties. Physical properties can include diameter, length, and density. Mechanical properties can include stiffness. Biochemical properties can include surface chemistry/ligand modification. Additional relevant properties can include biocompatibility and cell adherence. For example, it may be desirable for an artificial axon to be formed of materials that are biocompatible and cell adherent. Such features can enable other cells such as glial cells from the CNS to be seeded within the mimetic, adhere, grow, and respond to cues such as administered drugs.

Generally, axons are relatively uniform cylindrical projections of neuron bodies that travel together in bundles and have lengths that span multiple orders of magnitude. Although axon density varies widely across the CNS, extracellular space in white matter tracts is narrow, and axons lie in close proximity. A single oligodendrocyte has access to long segments of multiple axons in its vicinity. In the human brain, axon diameter generally varies from about 0.2 µm to about 9 µm, with a median diameter of about 0.6 µm [20].

The fibers of a cell-mimetic can be of axon-level diameter. For example, cell mimetic devices can include fibers having an average diameter of about 0.1 µm to about 20 µm (e.g., 0.08 µm, 0.09 µm, 0.2 µm, 0.3 µm, 0.5 µm, 0.6 µm, 1 µm, 1.5 µm, 2 µm, 3 µm, 4 µm, 5 µm, 6, µm, 7 µm, 8 µm, 9 µm, 10 µm, 15 µm, 20.1 µm, 20.2 µm), or of about 1 µm to about 10 µm (e.g., 0.9 µm, 1 µm, 1.5 µm, 2 µm, 3 µm, 4 µm, 5 µm, 5.1 µm, 6 µm, 7 µm, 8 µm, 9 µm, 10.1 µm, 10.2 µm), or of about 1 µm to about 5 µm (e.g., 0.9 µm, 1 µm, 1.5 µm, 2 µm, 3 µm, 4 µm, 5 µm, 5.1 µm), or of about 0.1 µm to about 5 µm (e.g., 0.08 µm, 0.09 µm, 0.2 µm, 0.3 µm, 0.5 µm, 0.6 µm, 0.8 µm, 1 µm, 2 µm, 5 µm, 5.1 µm), or of about 0.1 µm to about 2 µm (e.g., 0.08 µm, 0.09 µm, 0.2 µm, 0.3 µm, 0.5 µm, 0.6 µm, 0.8 µm, 1 µm, 2 µm, 2.1 µm), or of about 0.1 µm to about 1 µm (e.g., 0.08 µm, 0.09 µm, 0.2 µm, 0.3 µm, 0.5 µm, 0.6 µm, 0.8 µm, 1.1 µm). The diameter of fibers within a mimetic device can be uniform. Alternatively, a mimetic device can include fibers of varying diameters (e.g., fibers of two, three, four, five, or more differing diameters) and/or can include a gradient of fiber diameters (FIGS. 7A, 7D, 7F, 7G).

Mechanical characterization of brain matter suggests that neurons may be approximated as elastic solids [14] with an elastic modulus of about 0.1 kPa to about 1 kPa, which is very low as compared to the elastic modulus of most 3D printed thermoplastics, which are typically on the order of MPa to GPa.

Figure 7A:
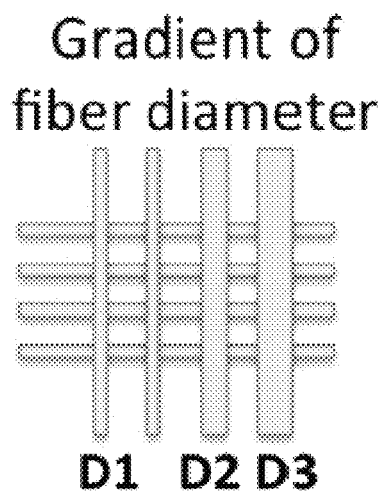
FIG. 7A is a schematic illustrating a gradient of fiber diameters.
Figure 7B:
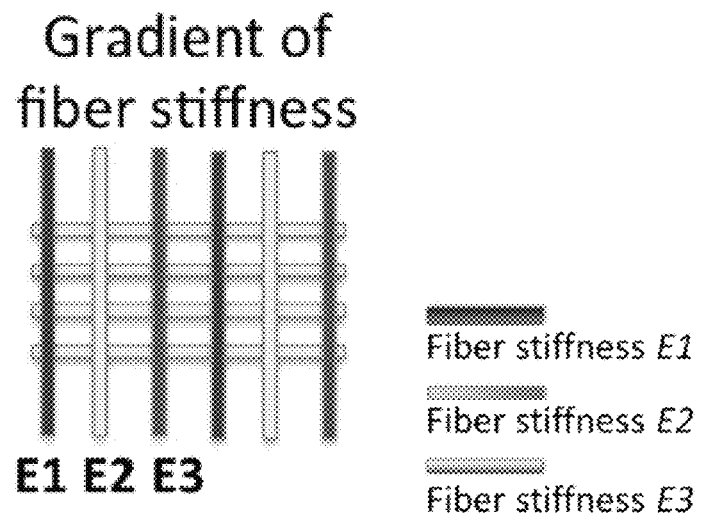
FIG. 7B is a schematic illustrating a gradient of fiber stiffness.
Figure 7C:
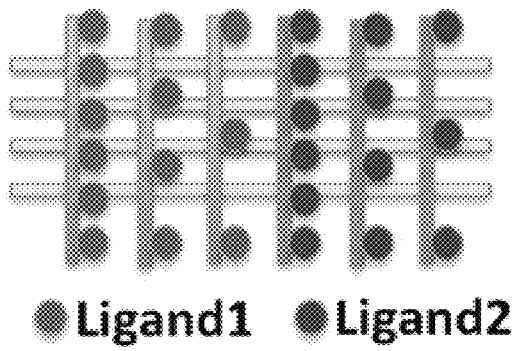
FIG. 7C is a schematic illustrating a gradient of ligand concentrations.
Figure 7D:
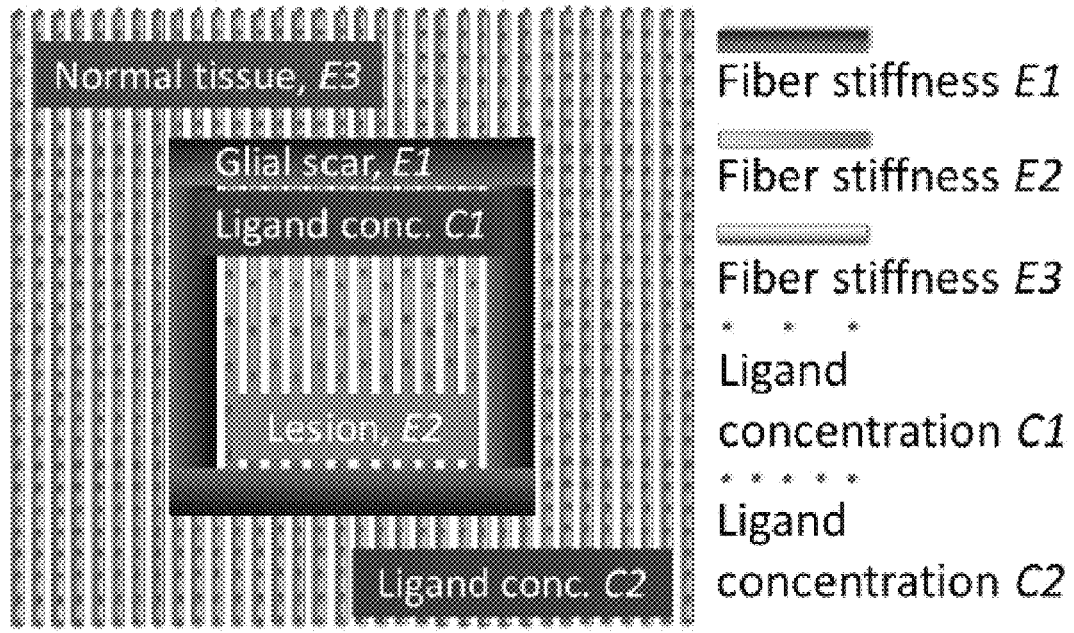
FIG. 7D is a schematic illustrating a complex fiber architecture (e.g. mimicking a demyelinating lesion).
Figure 7E:
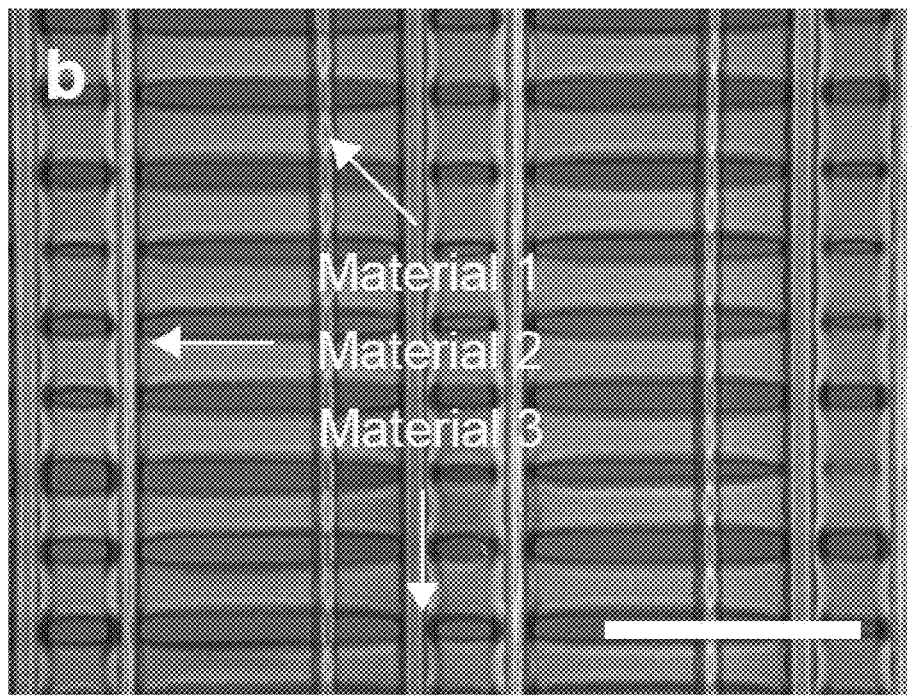
FIG. 7E is an image of a poly-HEMA fiber bundle including three distinct fiber inks corresponding to different stiffness.

The fibers of a cell-mimetic can be of axon-level stiffness. For example, cell mimetic devices can include fibers with an average stiffness (e.g., post-curing stiffness) of about 0.1 kPa to about 200 kPa (e.g., 0.08 kPa, 0.09 kPa, 0.2 kPa, 10 kPa, 20 kPa, 30 kPa, 50 kPa, 70 kPa, 90 kPa, 95 kPa, 105 kPa, 140 kPa, 150 kPa, 200 kPa, 220 kPa), or of about 0.1 kPa to about 50 kPa (e.g., 0.08 kPa, 0.09 kPa, 0.2 kPa, 5 kPa, 10 kPa, 10 kPa, 30 kPa, 40 kPa, 49.5 kPa, 50.1 kPa, 50.5 kPa), or of about 0.1 kPa to about 10 kPa (e.g., 0.08 kPa, 0.09 kPa, 0.2 kPa, 3 kPa, 5 kPa, 7 kPa, 9 kPa, 9.5 kPa, 10.1 kPa, 10.5 kPa), or of about 0.1 kPa to about 1 kPa (e.g., 0.08 kPa, 0.09 kPa, 0.2 kPa, 0.3 kPa, 0.5 kPa, 0.7 kPa, 0.9 kPa, 0.95 kPa, 1.05 kPa, 1.1 kPa). The stiffness of fibers within a mimetic device can be uniform. Alternatively, a mimetic device can include fibers of varying stiffness (e.g., two, three, four, five, or more different stiffnesses) and/or can include a gradient of fiber stiffness (FIGS. 7B, 7D, 7E).

As noted above, cell responses of interest with regard to myelination include both production and wrapping of myelin sheaths about axons. Cell-mimetic devices can include fibers that enable full-wrapping of myelin sheaths about the fibers' circumference. The fibers can be freestanding, for example, having no or few mechanical supports that obfuscate concentric wrapping. Schematics of artificial axons having features based on neuronal axons in CNS tracts are shown in FIGS. 1A-1B. Cell mimetics of the present invention can include fibers arranged horizontally, as shown in in FIG. 1A, or vertically, as shown in FIG. 1B. Horizontal fibers can have suspended portions located between supports that enable complete wrapping around the fibers' circumferences (see e.g., FIGS. 5A-C, 5E-G, 5I-K). The horizontal fibers can also be aligned, thereby more closely resembling axon bundles. The arrangement of horizontal fibers allows high throughput image acquisition of myelin segment lengths. Suspended fibers can include unsupported lengths of about 0.5 µm to about 1000 µm (e.g., 0.4 µm, 0.5 µm, 1 µm, 5 µm, 10 µm, 20 µm, 50 µm, 100 µm, 150 µm, 200 µm, 400 µm, 500 µm, 700 µm, 1000 µm, 1010 µm) or of about 10 µm to about 200 µm µm (e.g., 9 µm, 10

μm, 25 μm, 30 μm, 40 μm, 50 μm, 60 μm, 70 μm, 90 μm, 100 μm, 150 μm, 200 μm, 205 μm).

Vertical fibers, or pillars, as shown in FIG. 1B, can be freestanding fibers. Vertical fibers placed in close proximity can resemble the geometry of neuronal axons in axon bundles, while also allowing for fast detection of concentric myelin wrapping (see e.g., FIGS. 5D, 5H, 5L). Vertical fibers can have pillar heights of about 10 μm to about 1000 μm (e.g., 9 μm, 10 μm, 20 μm, 50 μm, 100 μm, 150 μm, 200 μm, 400 μm, 500 μm, 700 μm, 1000 μm, 1010 μm) or of about 20 μm to about 100 μm μm (e.g., 19 μm, 20 μm, 25 μm, 30 μm, 40 μm, 50 μm, 60 μm, 70 μm, 90 μm, 100 μm, 105 μm).

Figure 1C:
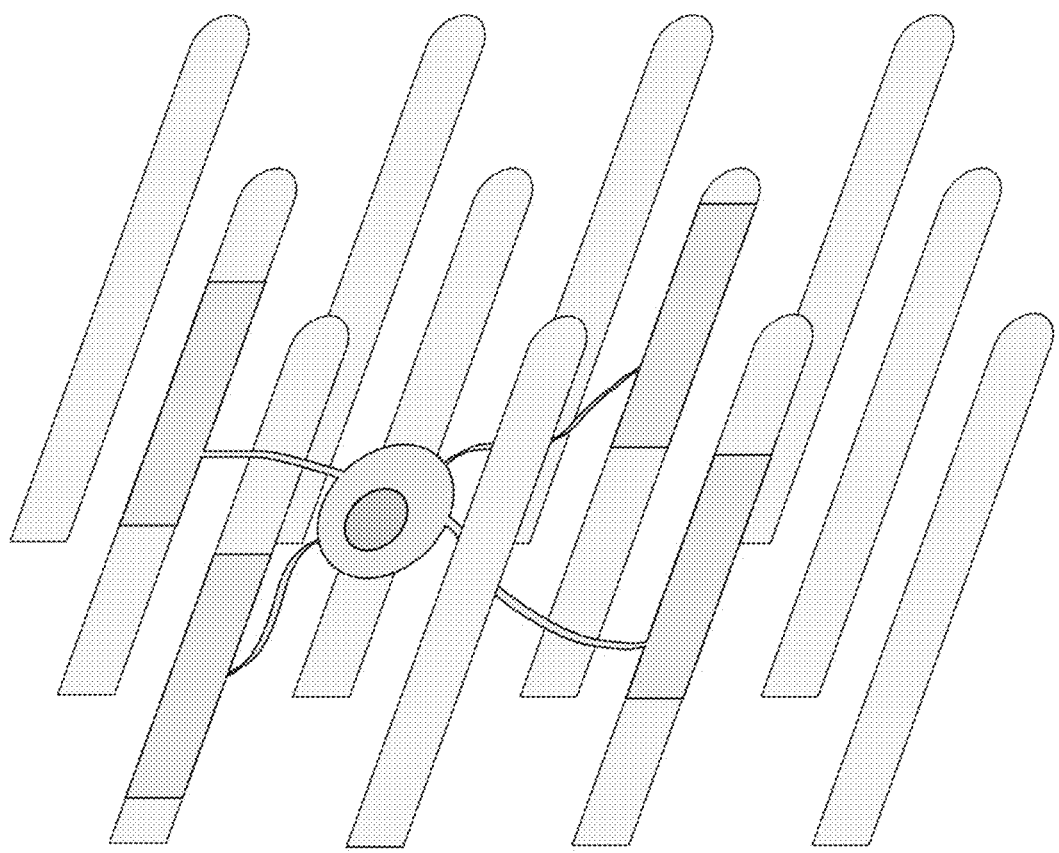
FIG. 1C is a schematic illustrating an example of artificial axons in an angled configuration including tilted freestanding fibers (e.g., pillars). Myelin, being wrapped around axon fibers by oligodendrocytes, is shown in green.

Vertical fibers can also include fibers that are substantially or partially vertical, such as freestanding fibers that are tilted at an angle between 0° and 90° with respect to a support of the array, for example, between about 10° and about 80° (e.g., 9°, 10°, 12°, 15°, 20°, 40°, 45°, 50°, 60°, 70°, 80°, and 81°) or between about 30° and about 60° (e.g., 29°, 30°, 35°, 40°, 45°, 50°, 55°, 60°, 61°). A schematic of tilted freestanding fibers are shown in FIG. 1C.

Cell mimetic devices can include fiber surfaces that are functionalized with proteins representing extracellular matrix (ECM) components and/or various ligands/receptors expressed on axon surface. For example, cell mimetics of the present invention can include fibers functionalized with laminin, fibronectin, Poly-D-Lysine (PDL), NCAM, ephrins, integrins, dystroglycans, contactins, or other surface ligands that are present in a cellular environment in vivo.

The diameter, stiffness, ligand concentration, ligand type, or any combination thereof, of the fibers of a cell-mimetic device can vary to mimic or to provide a model for a diseased environment. For example, a combination of fibers of different stiffnesses and ligand concentrations can be included in a cell mimetic device to provide a hypothetical model of a demyelinating lesion (FIG. 7D).

Manufacturing Methods for Cell-Mimetics

Cell-mimetics can be manufactured by additive printing techniques, also referred to as three-dimensional (3D) printing, to produce complex 3D architectures, such as pillar configurations and horizontally-arranged fiber configurations. Examples of additive printing methods for cell-mimetic devices follow.

Direct Ink Writing

A method of manufacturing a cell-mimetic device includes direct ink writing. Direct ink writing is a 3D printing technique that can overcome limitations typically arising with current lithography-based techniques. While lithography-based techniques enable fabrication of high aspect ratio, microscale features, the materials utilized in lithography-based techniques generally exhibit high mechanical stiffness. Such materials typically have elastic moduli on the order of MPa, which are not suitable for neuronal mimetics. Creating mechanically-compliant, unsupported features (e.g., horizontal fibers having suspended regions, vertical fibers in pillar configurations) by additive printing methods is particularly challenging due to the coupling of materials of low elastic moduli, demolding mechanics, and operating conditions that often induce structural collapse and/or deformation [21, 22, 23].

Direct ink printing, in which a material is extruded through a fine nozzle into a predefined, programmed shape, can overcome such challenges, as further described in International Pub. No. WO/2017/147501, the entire contents of which are incorporated herein by reference [24].

Figure 2A:
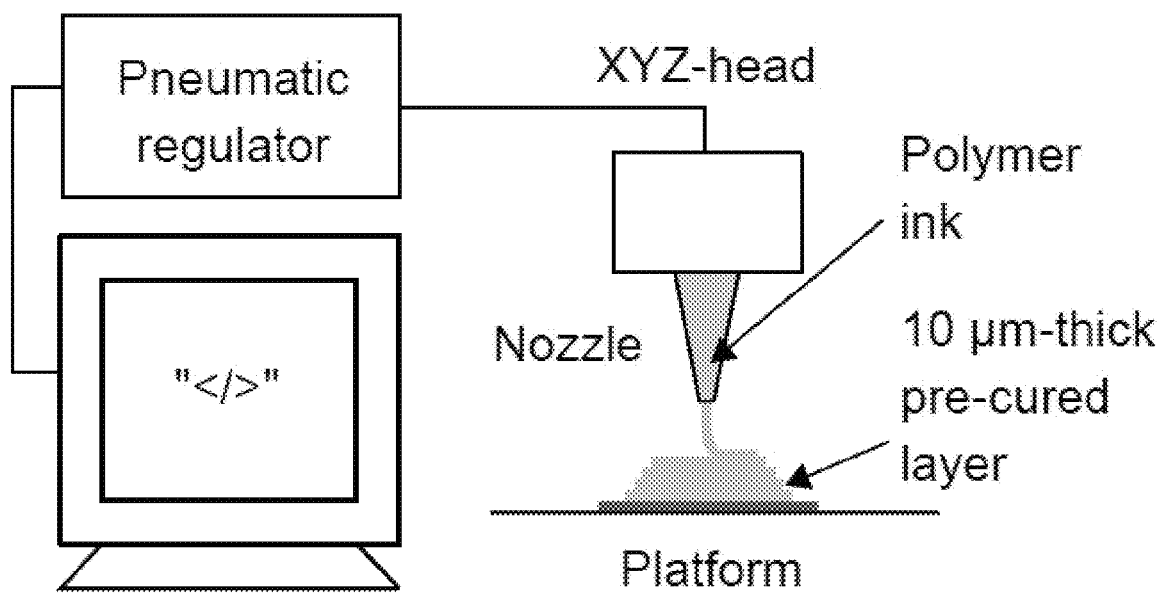
FIG. 2A is a schematic illustrating a system for direct ink printing.

An example of a 3D printing technique is shown in FIG. 2A. Specifically, fiber-like constructs, or lattices, composed of spanning cylindrical features (e.g., fibers having suspended regions) with micron scale diameters, are extruded from a nozzle of a direct ink printer. The printer can include a pneumatic regulator to control a flow of ink through the nozzle and a processor to provide programmatic control of the printing process, including, for example, controlling a position of a translational head having the nozzle and controlling a flow rate of the ink. Upon deposition onto a platform or substrate, the 3D constructs are cured, such as by UV or thermal curing. With 3D printing, complex architectures can be created whose local composition, geometry, and mechanical stiffness can be programmably defined.

However, the rheological characteristics of the extruded material (e.g., polymer "inks") for direct ink printing can be challenging for cell mimetics. Generally, polymer inks must be able to withstand high shear stresses, and materials currently utilized for most 3D printing techniques have high elastic moduli upon curing. Inks particularly suited to producing cell mimetics by direct ink writing are described further below. Such inks are tailored to facilitate flow through a deposition nozzle under an applied shear stress, yet retain filamentary shape upon exiting the nozzle.

Projection Microstereolithography

Cell-mimetic devices can alternatively be manufactured by projection microstereolithography (PμSL) methods. PμSL offers unique advantages for creating 3D microstructures with submicrometer spatial resolution (e.g., about 0.5 μm), high vertical aspect ratios, and/or suspended or freestanding parts. PμSL also offers flexibility with regard to choices for biocompatible and biodegradable polymer and resin precursors [25].

Figure 2B:
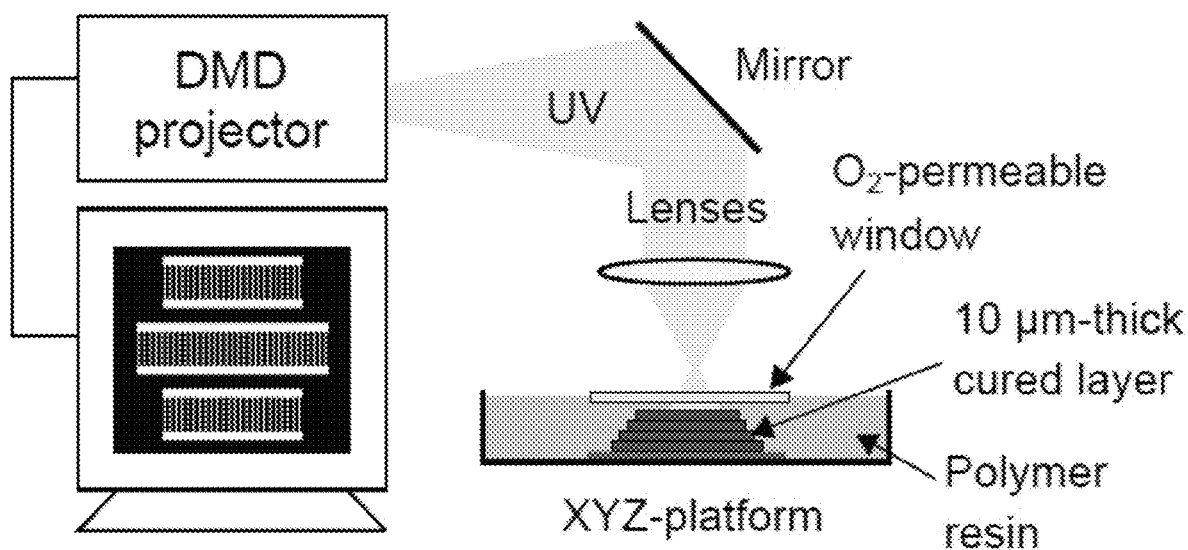
FIG. 2B is a diagram illustrating a system for Projection Microstereolithography (PμSL).

An example of a PμSL technique is shown in FIG. 2B. Specifically, in PμSL methods, computer generated digital images replace the physical masks associated with conventional lithography. Slices of a 3D CAD model are sequentially sent to a digital micromirror device (DMD) illuminated by a light source and projected through an oxygen permeable window unto a photopolymer resin bath. The resin bath can be placed on a translation platform, which can also be controlled by the processor. Microstructures are built in a layer-by-layer manner through sequential projection of CAD model slices and translation of the resin bath.

PμSL can provide for high fabrication speeds and low costs. Light intensity and exposure time can be adjusted to vary the crosslinking density of the polymer material, allowing for variation in elastic modulus, viscosity, permeability, and swelling ratio. Modular arrays of cell mimetics can be produced having high aspect ratios in both horizontal and vertical fiber configurations. The fiber arrays can be fabricated on glass coverslips functionalized with a silane-coupling agent to facilitate immobilization of the constructs on a rigid and transparent substrate.

In stereolithography, a fast print speed can be obtained while high feature resolution is retained by controlling oxygen inhibition above the cured sample surface. Accordingly, an oxygen permeable window can be placed above the UV projection plane (or below, as in inverted PμSL systems) to maintain a thin layer of uncured resin between the window and the cured sample throughout fabrication. Separation forces between the window and the cured sample can be very large and destructive to the sample. Separation of parts becomes increasingly problematic in PμSL with increased material hydrophilicity and low mechanical stiffness, and separation forces remain large even with the use of PDMS windows. Alternative coatings to PDMS, such as fluoropolymers, can reduce the magnitude of separation forces as well as prevent absorption of resin components, which can significantly improve curing time and resolution.

Further, two-photon stereolithography can be used as an alternative to fabricate sub-micron artificial axons, using the same materials and similar approach. The quadratic dependence of two-photon absorption confines the photopolymerization to nano-volumes, which can allow for artificial axons with physiological dimensions closer to those found in the human CNS, such as, for example about 0.5 μm to about 1.0 μm.

Materials for Additive Manufacturing

In some embodiments, materials of the present invention relate to a library of biocompatible polymers that are suitable for extrusion-based direct printing and PμSL methods of cell-mimetics. The elastic moduli of fibers printed with these materials can range from, for example $10^2$ to $10^6$ Pa, orders of magnitude below current state-of-art materials used in glial cultures and myelination assays. Examples of current state-of art materials include polystyrene, polycaprolactone, and poly-lactic acid, which have elastic moduli of $10^7$ to $10^9$ Pa [26, 27].

Materials for each of the cell-mimetic manufacturing methods described above are discussed in turn. In particular, two types of ink for fiber production by extrusion-based 3D printing have been optimized, and a new copolymer ink compatible with PμSL has been developed. These inks, as compared with current state-of-art materials, are shown in FIG. 3A, with pHEMA-, PDMS-, and HDDA-based inks shown to the left of the vertical line, and current state-of-art materials shown to the right of the vertical line.

Figure 3A:
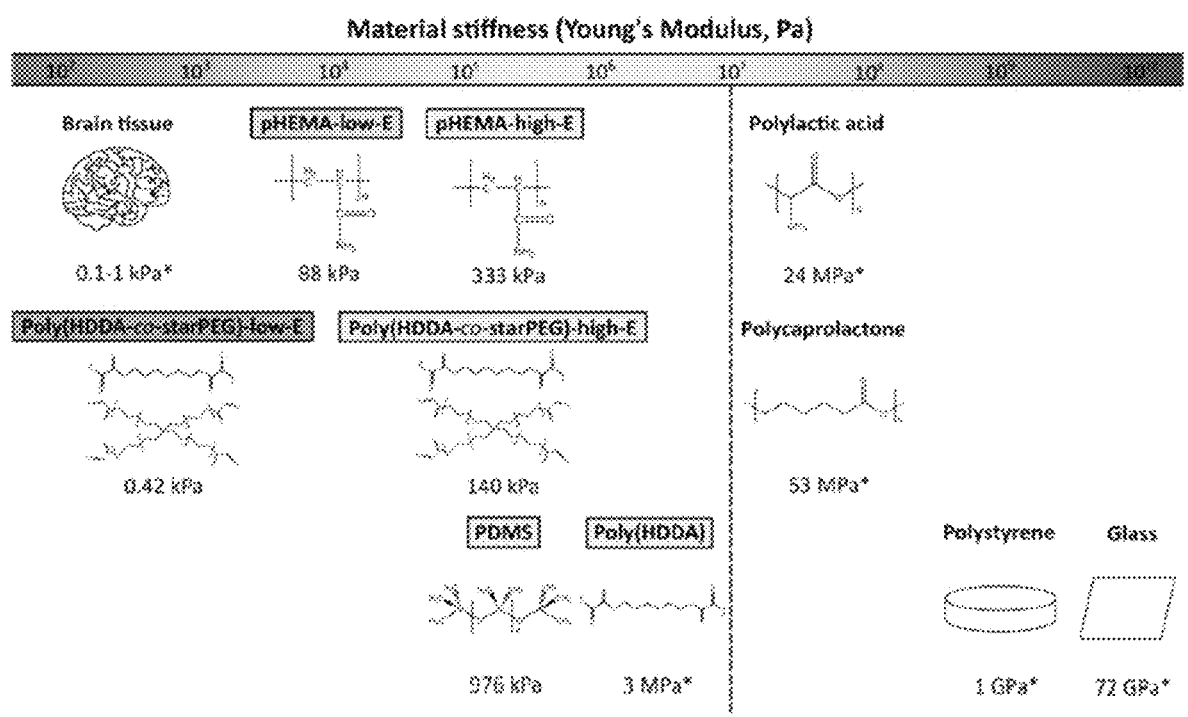
FIG. 3A is a chart illustrating relative stiffness of additive manufacturing materials.

As shown in FIG. 3A, materials for the additive manufacturing of artificial axons, with stiffness of less than about $10^7$ Pa, provide for mimetics having a mechanical stiffness more similar to CNS tissue, while state-of-art materials, with stiffnesses of more than about $10^7$ Pa, currently used for myelination assays are significantly stiffer than CNS tissue.

Direct Ink Printing Materials

As noted above, materials for direct ink printing pose several challenges. Polymer inks that have been produced for direct writing include inks based on polyelectrolytes, polydimethylsiloxane (PDMS), and poly(2-hydroxyethyl methacrylate) (pHEMA) [22, 23, 28]. However, such polymer inks, while able to withstand high shear stresses, have high elastic moduli upon curing.

Examples of polymer ink components for direct ink printing materials that can more closely provide for optimized fiber properties are further described in International Pub. No. WO/2017/147501, the entire contents of which are incorporated herein by reference [24].

For fiber production with extrusion-based 3D printing, new PDMS-based (SE1700, Dow Corning) inks that form elastic and deformable fiber arrays and new pHEMA-based inks that form viscoelastic hydrogels after hydration have been created. As further described in Examples 2 and 9 herein, PDMS fibers with diameters of 10 μm were achieved that spanned lengths of 200 μm and had a Young's modulus, E, of 976±11 kPa. Also, as further described in Examples 3 and 9 herein, two pHEMA inks, each with a different Young's modulus, were developed, from which suspended fibers having diameters of 5 μm and 10 μm were achieved. The inks included a relatively low stiffness ink (E=88±10 kPa) and a relatively high stiffness ink (E=333±30 kPa).

PDMS-based inks can comprise a PDMS base (e.g., SE1700 Clear base, Dow Corning, Midland, Mich.) of about 80% to about 99% w/w, or about 85% to about 95% w/w, or of about 90% w/w. A remainder of the ink can comprise a hardener, such as e.g. SE1700 Catalyst, Dow Corning, Midland, Mich., and fluorescent dye (e.g., 0.01% w/w rhodamine).

pHEMA-based inks can comprise about 5% to about 15% of 1000 kDa pHEMA or about 10% 1000 kDa pHEMA and about 20% to about 30% of 300 kDa pHEMA or about 25% 300 kDa pHEMA. In addition, pHEMA-based inks can comprise HEMA monomer. For high-E inks, about 30% to about 50% of HEMA monomer, or about 40% of HEMA monomer can be included. For low-E inks, about 2% to about 10% of HEMA monomer, or about 5% of HEMA monomer, can be included. The inks can further comprise about 0% to about 5% EDGMA (co monomer), or about 1% EDGMA. The inks can further comprise a solvent, such as ethanol or water.

PμSL Printing Materials

For fiber production by PμSL techniques, copolymer inks were developed to achieve desired printing and cell compatibility properties. For PμSL techniques, resins that are liquid at room temperature, of low viscosity, and capable of curing quickly and locally under UV light are desirable. Hexanediol diacrylate (HDDA) is commonly used in stereolithography-based additive manufacturing to yield three-dimensional structures with mechanical stiffness that is approximately two orders of magnitude below that of polystyrene and glass. However, HDDA is known to have limited compatibility with oligodendrocytes [29]. Also, HDDA printed structures are sensitive to solvent changes and aqueous conditions, likely due to the high hydrophobicity of this material and surface tension phenomena, as further described in Example 13. Furthermore, silane coupling between HDDA microstructures and glass is inefficient, resulting in lifting and peeling of printed constructs during post-fabrication processing and in cell culture conditions.

Figure 3B:
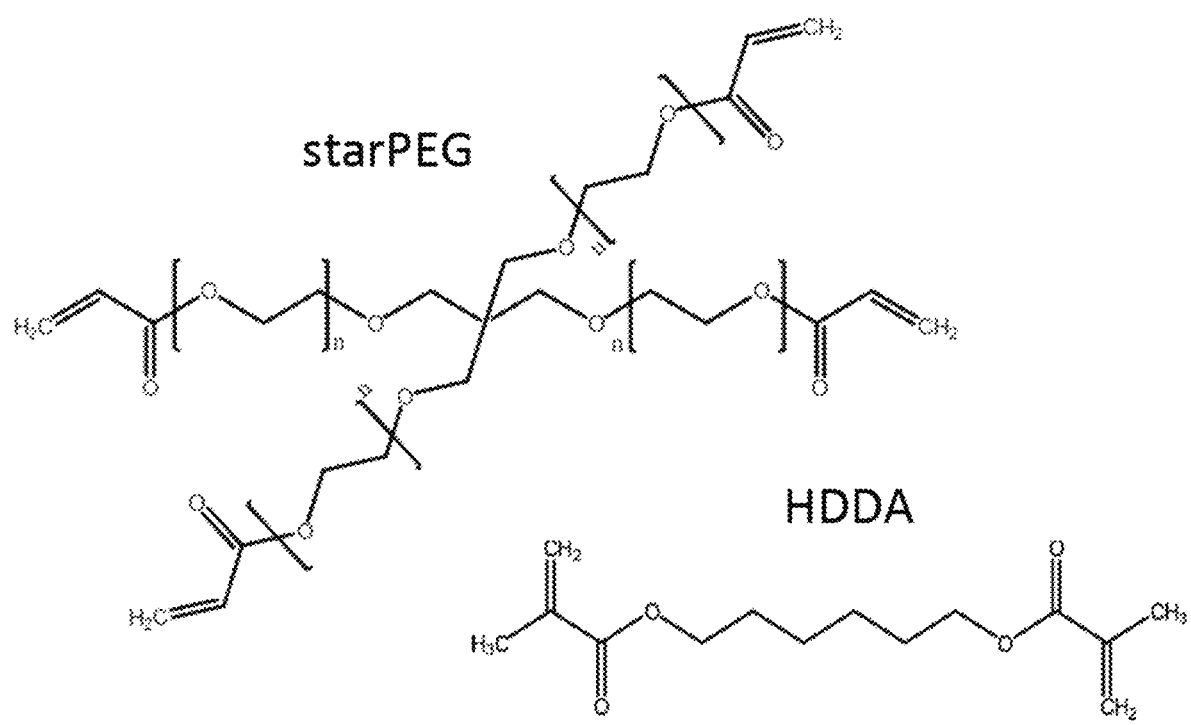
FIG. 3B illustrates HDDA and starPEG.

A new material system was developed for artificial axons that provides for materials having elastic moduli on the order of 0.1-200 kPa. The new material can comprise HDDA or an HDDA derivative and at least one derivative of polyethylene glycol (PEG), such as, for example, PEG-acrylate, PEG-diacrylate, or any multi-arm PEG-acrylate. In one embodiment, the material is poly(HDDA-co-starPEG). The copolymerization of HDDA with traditionally biocompatible and compliant PEG polymer precursors mitigates the challenges that preclude HDDA implementation in biological applications while retaining capability for POL fabrication techniques. As further described in Examples 4 and 9 herein, poly(HDDA-co-starPEG) resins with varying elastic moduli were developed, including resins with relatively high stiffness (E=140±35 kPa) and resins with relatively low stiffness (E=0.42±0.14 kPa). FIG. 3B illustrates the chemical structures of HDDA and starPEG.

Poly(HDDA-co-starPEG)-based inks can comprise about 1% to about 20% w/w of HDDA, or about 10% w/w HDDA, for low-E inks, and about 20% to about 99% w/w of HDDA, or about 30% w/w HDDA for high-E inks. In addition, the inks can comprise starPEG at about 1% to about 99% w/w, or at about 10% w/w. The inks can further comprise a solvent, such as Dimethyl sulfoxide (DMSO).

Figure 4C:
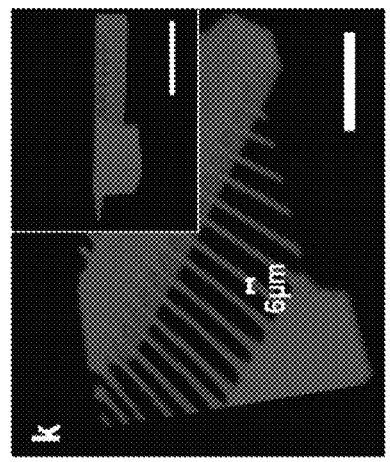
FIG. 4C is an image of an example of a digital mask for printing of horizontal fibers by PμSL.
Figure 4G:
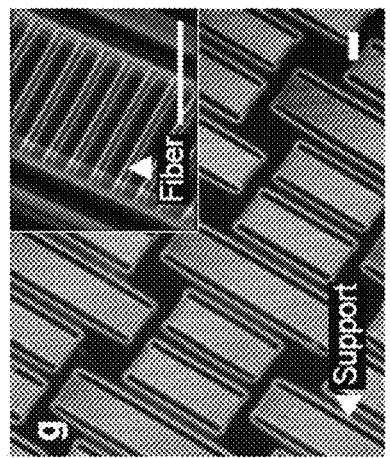
FIG. 4G is a phase contrast microscope image of a fabricated sample of horizontal fibers printed by PμSL with the digital mask of FIG. 4C.
Figure 4D:
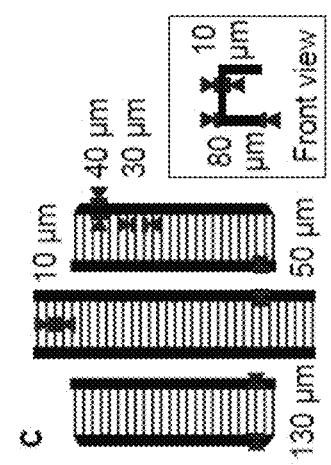
FIG. 4D is an image of an example of a digital mask for printing of vertical fiber pillars by PμSL.
Figure 4K:
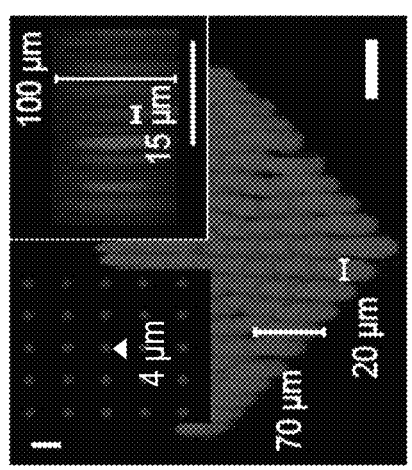
FIG. 4K is a confocal microscopy image of the fibers of FIG. 4G. Scale bars are 100 μm.
Figure 4H:
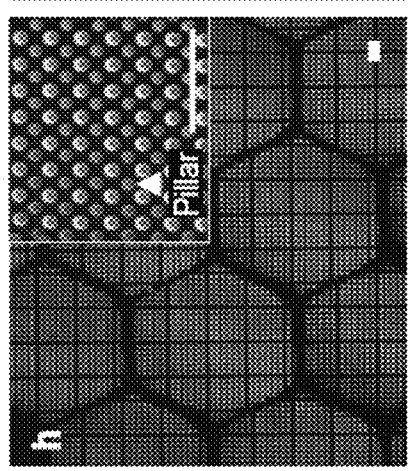
FIG. 4H is a phase contrast microscope image of a fabricated sample of vertical fiber pillars printed by PμSL with the digital mask of FIG. 4D.
Figure 4L:
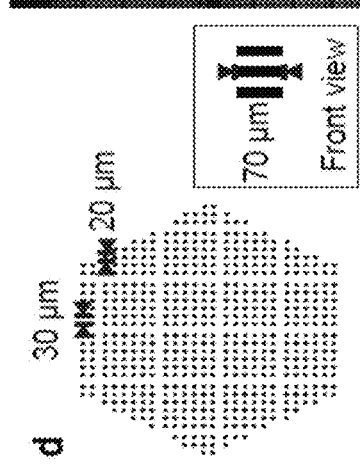
FIG. 4L is a confocal microscopy image of the fibers of FIG. 4H. Scale bars are 100 μm.

Cell mimetics with horizontally arranged fibers were printed using PμSL techniques and poly(HDDA-co-starPEG) materials (FIGS. 4C, 4G, 4K). The devices included suspended fibers having a uniform diameter of about 4 μm to about 20 μm and suspended lengths spanning over 100 μm. Additionally, vertically oriented and compliant fibers with uniform diameters of about 4 μm to about 20 μm and pillar heights of about 70 µm to about 100 µm were also printed using POL techniques and poly(HDDA-co-starPEG) material (FIGS. 4D, 4H, 4L).

Horizontally arranged fibers having unsupported regions spanning over 100 µm mimic physiological internode lengths for myelinating oligodendrocytes, while vertically aligned pillars are convenient for rapid quantification of myelin production. As noted by Mei et al. [13], a vertical orientation enables facile microscope documentation of apparent myelin sheath around the pillar perimeter. However, confirmation of such three dimensional wrapping can require visualization of a fiber over a finite distance along its longer dimension, such as by confocal scanning. Fibers and pillars of the present invention can be fabricated in modules of patterned arrays. For example, printed fields measuring up to 1×1 mm, total construct dimensions of 6×6 mm, and overall target sample thicknesses of 70-100 µm were created. However, the length, spacing, and diameter of printed fibers in a fiber array can be modified by adjusting a projection mask for the PµSL process.

Cell Mimetic Devices

Cell mimetic devices of the present invention (e.g., as printed by direct ink writing, and PµSL methods and materials) can provide for artificial axon arrays with fibers that are mechanically compliant (e.g., having a stiffness of about 0.1 kPa to about 200 kPa), aligned and minimally supported, and of diameters matching those of neural cells (e.g., about 0.1 µm to about 20 µm). Although multiple cues modulate cell behavior, the capacity to create such cylindrical fiber arrays with mechanical stiffness approaching that of neuronal axons can enable further understanding of how the mechanical environment of glial cells affects differentiation/myelination in health and disease.

As further described below in Examples 1-15 herein, cell mimetic devices were fabricated by additive manufacturing techniques described above to produce artificial axons. In short, PDMS fibers with a diameter of 10 µm and an unsupported length of 200 µm were achieved by direct-ink writing methods (FIGS. 4A, 4E, 4I). Multi-layered fiber bundles of pHEMA fibers with a diameter of 5-10 µm and spanning lengths of 30-60 µm were also achieved by direct-ink writing methods (FIGS. 4B, 4F, 4J). Using PµSL methods and materials, horizontal and vertical arrangements of fibers having predetermined diameters of 4-20 µm and lengths of 70-130 µm were achieved (FIGS. 4C, 4D, 4G, 4H, 4K, 4L).

It was further confirmed that OPCs could adhere to, migrate along, and efficiently differentiate into myelinating oligodendrocytes on the fabricated artificial axons (FIGS. 5A-5L). Moreover, OPCs differentiated into MBP+ oligodendrocytes that ensheathed fibers with up to 120 µm-long segments wrapped around entire fiber circumferences.

The ability to independently manipulate characteristics of individual neuronal axon-mimicking fibers, fiber arrays, and the surrounding environment can enable systematic interrogation of individual cues on oligodendrocyte response and myelinating. The tunability of cell mimetics and its effect on myelin wrapping was demonstrated by varying fiber diameters in both horizontal and vertical arrays, mechanical stiffness of the fiber material, and fiber surface coating (FIGS. 6A-6G).

Figure 6A:
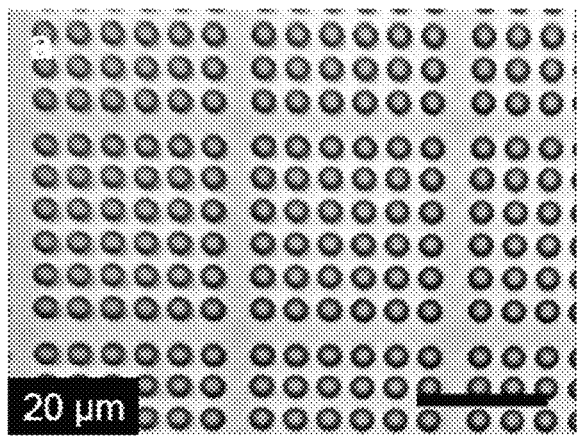
FIG. 6A is an image of fibers fabricated in a vertical pillar configuration by PμSL with a diameter of 20 μm. Scale bar 100 μm.
Figure 6B:
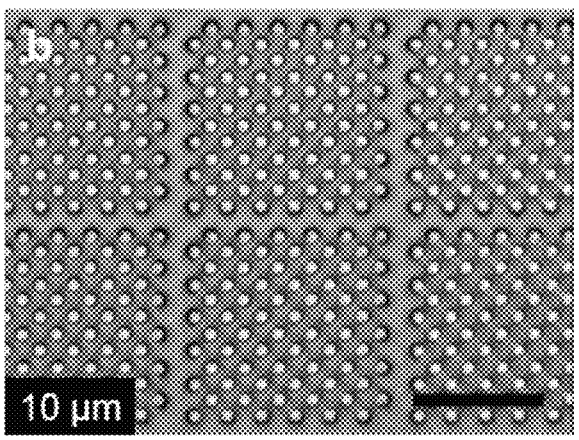
FIG. 6B is an image of fibers fabricated in a vertical pillar configuration by PμSL with a diameter of 10 μm. Scale bar 100 μm.
Figure 6C:
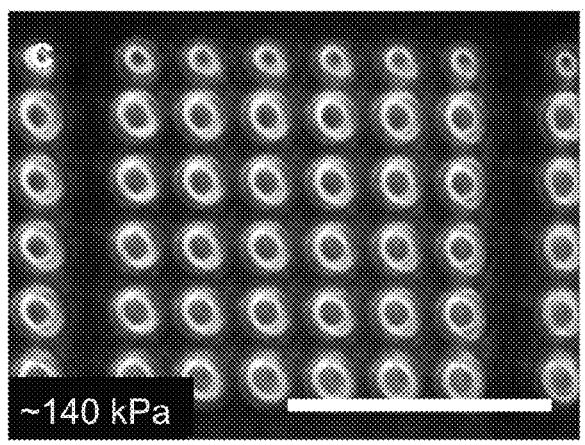
FIG. 6C is an image of fibers fabricated in a vertical pillar configuration by PμSL with a stiffness of about 140 kPa. Scale bar 100 μm.
Figure 6D:
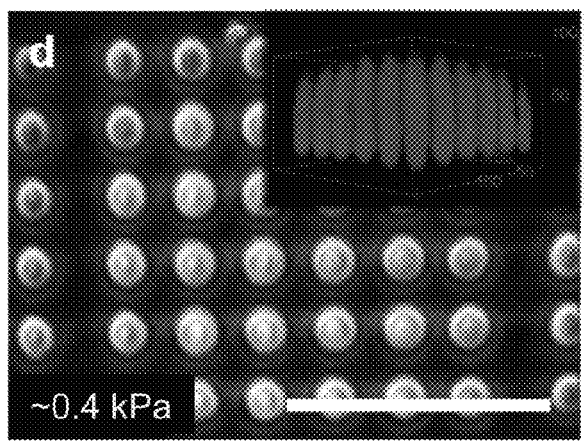
FIG. 6D is an image of fibers fabricated in a vertical pillar configuration by PμSL with a stiffness of about 0.4 kPa. Scale bar 100 μm.
Figure 6E:
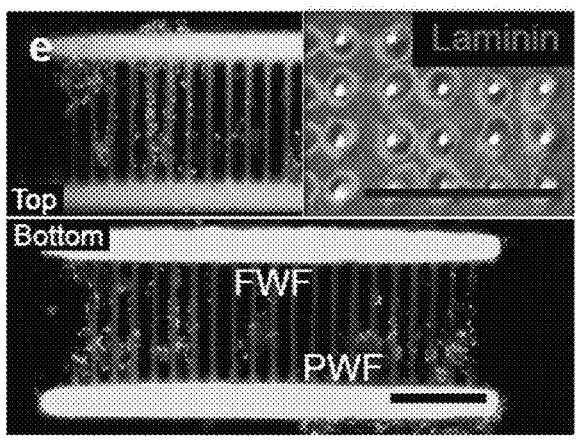
FIG. 6E is an image of top and bottom views of fibers fabricated in a horizontal configuration by PμSL that are sufficiently hydrophilic to enable a high extent of physiosorption of specific protein ligand laminin. Scale bar 100 μm.
Figure 6F:
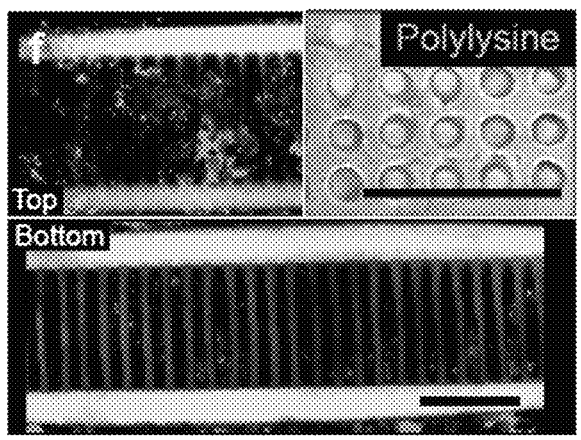
FIG. 6F is an image of top and bottom views of fibers fabricated in a horizontal configuration by PμSL that are sufficiently hydrophilic to enable a high extent of physiosorption of non-specific peptide ligand poly-D-lysine. Scale bar 100 μm.
Figure 6G:
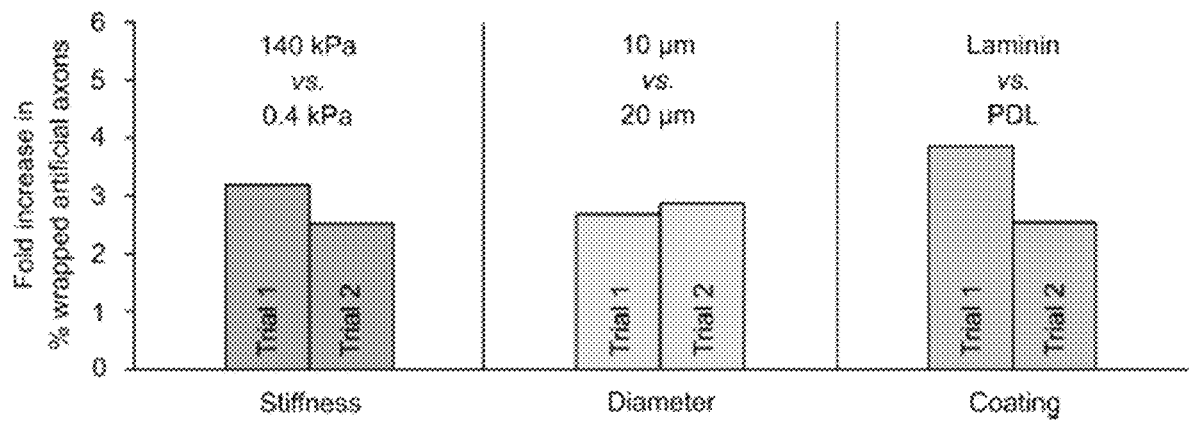
FIG. 6G is a graph illustrating measured effects of artificial axon stiffness diameter on vertical fibers (e.g. pillars), and ligand coating on horizontal fiber wrapping with myelin membrane. Fully wrapped fibers were defined as fibers having at least 80% of fiber circumference wrapped and covered by MBP+ segments along top and bottom lengths of at least 30 μm. The bars show the relative fold increase of the percent of fully wrapped fibers for each condition, for two independent experiments. Increased wrapping occurred for stiffer (140 kPa vs 0.4 kPa), thinner (10 μm vs 20 μm) and laminin coated fibers.

The versatility of the methods and materials described herein allows for the manipulation of physical, biochemical, and mechanical properties of artificial axons with high control and precision. As one example of how such variations can modulate myelination response, it was shown that significantly more ensheathment occurred for oligodendrocytes engaging stiffer, thinner and laminin-coated vs. poly-D-lysine-coated artificial axon arrays (FIG. 6G). Interrogation of the myelin sheath can be further facilitated by materials and methods of the present invention in conjunction with two- and three-dimensional imaging methods, such as fluorescence microscopy, confocal microscopy, scanning electron microscopy and/or x-ray microtomography.

Cell-mimetic devices that include arrays of fibers can be created in varying sizes and can serve as platforms for myelination assays to assess potential therapeutic compounds. Such arrays can include fibers of realistic stiffness, cylindrical geometry, and spacing of biological axons as the target for glial cell myelinating response. The robustness of the methods of the present invention enables the generation of a large number of samples with variation of single or multiple features, to generate customized assays for high-throughput experiments. A high degree of fiber alignment and uniformity throughout an array is amenable to high-throughput analysis, to gather complete information regarding extent of wrapping and segment length.

Disease microenvironments often present complex structure of biochemical and biophysical features, whose spatial arrangements may be important factors in a disease. For example, tumor or demyelinating lesion environments demonstrate spatial gradients of stiffness and acidity, as well as changes in cellular composition and molecular components of ECM [19, 30, 31, 32, 33]. It has been demonstrated that oligodendrocyte lineage cells are strongly mechanosensitive and many aspects of their biology, including survival, proliferation, migration and differentiation depends on mechanical cues such as substrate stiffness and mechanical strains [17, 34]. It has also been shown that acidic pH in inflammatory lesions may decrease OPC survival, proliferation, migration speeds and differentiation, and that pH gradient drives OPC migration toward the acidic pH [32]. Therefore, the ability to incorporate such components of an OPC environment into assays can advantageously enable more predictive drug screenings. Traditional in vitro assays are challenged to recreate such complexity of a cell microenvironment in a reproducible and resource-effective manner. In contrast, cell-mimetics of the present invention and additive manufacturing methods for creating such cell-mimetics can provide for the ability to combine different materials, stiffnesses, geometries, and surface chemistries in a controllable manner, which, in turn, can provide for mimicking the complexity of a disease environment more credibly, and at the same time provide for the generation of assays in a highly reproducible manner. In the Examples below, cell-mimetics and methods of making cell-mimetics are described that demonstrate the ability to print fibers of varying diameters and stiffness within the ranges typical of biological axons. As further described in the Examples below, it was demonstrated that oligodendrocytes can fully wrap the fibers of such cell-mimetics and can wrap the fibers in a property-dependent manner. Through a combination of materials and array architectures, such as those described herein, in vitro assays can provide better mimics of different disease microenvironments than currently-available devices.

EXEMPLIFICATION

Example 1: Purification and Culture of Rat Oligodendrocyte Precursor Cells

OPCs were isolated from Sprague Dawley rat mixed glial cultures. Briefly, mixed glial cultures obtained from neonatal cultures were maintained for 10-14 days in 10% fetal bovine serum (FBS, Atlanta Biologicals) and DMEM (Gibco) and shaken overnight at 37° C. and 5% C02 to detach OPCs. After shake-off, OPCs were purified from microglia in P60 dishes by differential adhesion to untreated polystyrene. OPCs were maintained in progenitor state in DMEM with SATO modification (5 mg/mL insulin, 50 mg/mL holo-Transferrin, 5 ng/mL sodium selenate, 16.1 mg/mL putrescine, 6.2 ng/mL progesterone, and 0.1 mg/mL bovine serum albumin), 10 ng/mL platelet-derived growth factor homodimer AA (PDGF-AA, Peprotech) and 10 ng/mL basic fibroblast growth factor-2 (FGF-2, Peprotech) (proliferation medium). Differentiation was induced after 24 h-48 h in SATO's medium with 0.5% FBS, without PDGF-AA and FGF-2 (differentiation medium).

Example 2: Fabrication of PDMS Fibers

Figure 9:
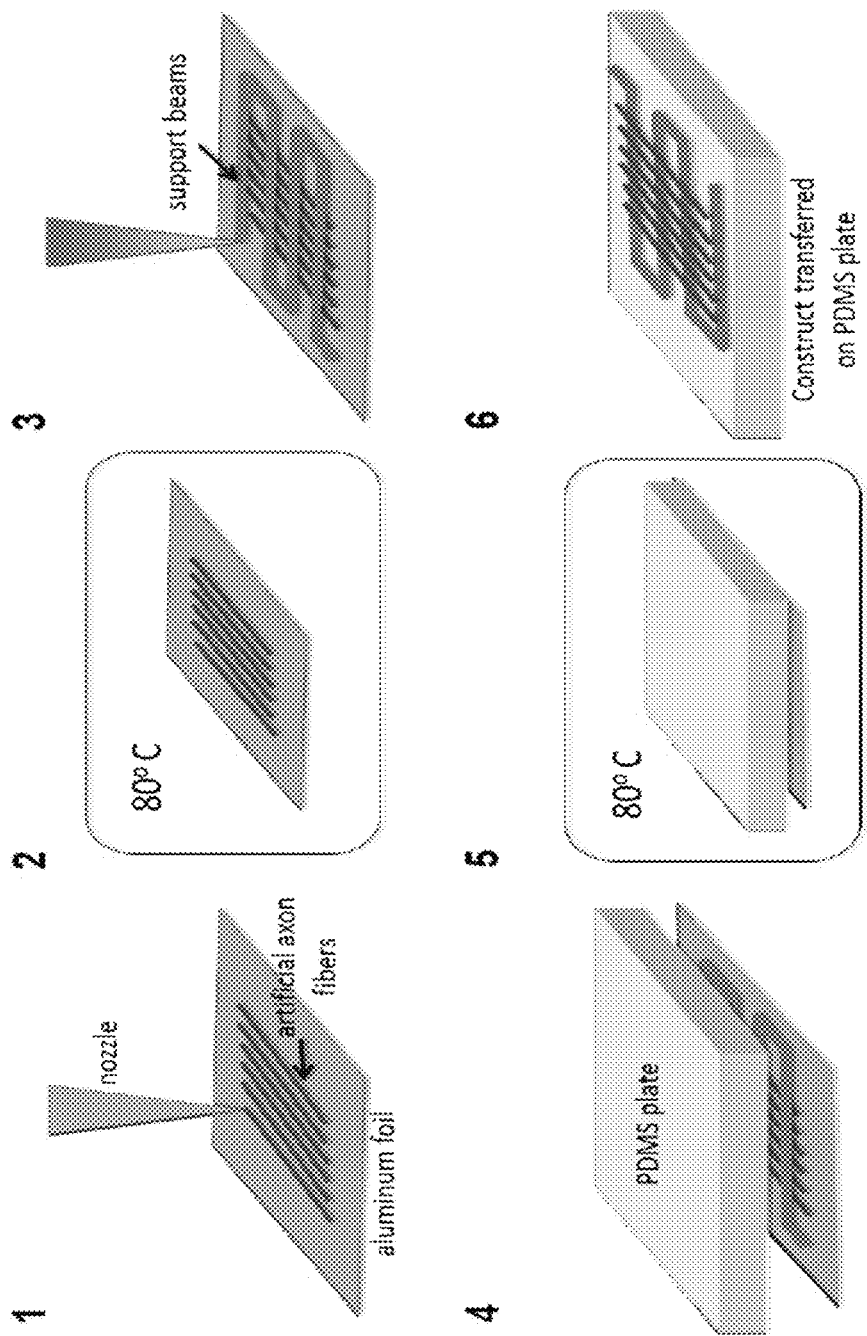
FIG. 9 is a schematic illustrating a series of PDMS fiber printing steps.

Substrate:
PDMS fibers were first printed on a layer of smooth aluminum foil, and then transferred onto glass slides or custom-made PDMS plates, as shown in FIG. 9.
Resin:
PDMS ink was made using SE1700 (Dow Corning), 10:1 w/w base to hardener ratio, and 0.01% w/w Rhodamine B as a fluorescent marker for fiber imaging. Components were mixed in a centrifugal deaerating mixer (Thinky Mixer) for 6 min, then loaded into the syringe, spun for 10 min in the centrifuge for degassing, and used immediately.
Fabrication:
A syringe with degassed ink was mounted on a custom 3D printing setup; the ink was extruded through a glass nozzle with 10 μm inner diameter. The top layer of fibers was first printed on the smooth aluminum foil and pre-cured for 30 min at 80° C. to stabilize the shape (FIG. 9, steps 1 and 2), followed by printing supporting beams with 200 μm diameters on top of the procured fibers (FIG. 9, step 3). The fibers were then sandwiched with either a glass slide or PDMS custom plate, and cured at 80° C. for 2 h (FIG. 9, steps 4 and 5). After curing, the top layer of aluminum was gently removed, leaving behind the undisturbed top layer of fibers (FIG. 9, step 6). This "top-to-bottom" printing technique with pre-curing step allowed for the production of suspended fibers. If printed directly on the support beam, PDMS fibers with diameters as small as 10 μm sag and collapse to the substrate surface before curing.

Example 3: Fabrication of Poly-HEMA Fibers

Substrate:
Poly-HEMA fibers were printed on clean glass slides.
Resin:
pHEMA inks were prepared with varying concentrations of high molecular weight pHEMA chains (1 MDa and 300 kDa, Sigma-Aldrich), HEMA monomer (Sigma-Aldrich), ethylene glycol dimethacrylate (EGDMA) comonomer (Polysciences), Irgacure 2959 photoinitiator (BASF), ethanol, and deionized water (FIG. 8A). Each ink was produced by first combining all the liquid components with Irgacure until it is dissolved using brief (15 s) sonication; the solid components were then added (high molecular weight pHEMAs). The mixture was placed in a 20 mL centrifugal mixing container (Thinky mixer), mixed at 2000 rpm for 5 min, and left to sit in a light-free container for 72 h at 4° C. where the pHEMA chains relax and disperse in the solvent to create a highly viscous ink. Finally, the pHEMA ink was loaded into a UV-proof syringe and spun in the centrifuge for degassing. The ink can be used immediately or stored protected from light in 4° C. for up to 6 weeks.
Fabrication:
pHEMA fibers were printed as multi-layer logpile constructs directly on glass slides using a tapered glass nozzle with 5 or 10 μm inner diameter. The fibers maintain their suspended shape before curing allowing for printing of multiple fiber layers without a pre-curing step. Printed constructs were then UV-cured using an Omnicure UV, and stamped to the glass substrate with a rim of PDMS, which was next thermally cured. The cured constructs were washed in sterile water for 7 days, before functionalization for cell culture.

Example 4: Fabrication of Poly(HDDA-Co-starPEG) Fibers

Substrate:
Poly(HDDA-ca-starPEG) fibers were fabricated on functionalized 12-mm coverslips. Coverslips were rinsed with acetone and ethanol to remove impurities, blown dry with air, and exposed to air plasma for 5 minutes. Activated coverslips were functionalized with 2% v/v 3-(Trimethoxysilyl)propyl methacrylate (Sigma-Aldrich) and 1% v/v acetic acid in ethanol at room temperature for 2 h, to introduce acrylate groups on the surface that bind to the photopolymerized structures during PμSL fabrication. Coverslips were subsequently rinsed twice with ethanol, blown dry, and stored in a desiccator for up to 6 months.
Resin:
Poly(HDDA)-starPEG-high-E resin was prepared by mixing 10% w/w 4-arm PEG acrylate (starPEG, 20 kDa arms, Creative PEGWorks), 30% w/w HDDA (Sigma), 2% w/w Irgacure 819 (phenylbis(2,4,6-trimethylbenzoyl)phosphine oxide, Sigma), 0.7% Sudan I (Sigma) and 0.1% Rhodamine B (Sigma) in DMSO, and sonicating at 37° C. for 10 min. Poly(HDDA)-starPEG-low-E resin was prepared similarly, with 10% w/w 4-arm PEG acrylate and 10% w/w HDDA. Resins were stored in opaque containers at room temperature for up to 3 months.
Fabrication:
Fabrication of fibers and pillars was enabled by the POL apparatus specifically tailored for printing micrometer scale features using compliant materials. A CAD model was sliced to obtain cross-sectional images of the 3D structure at different heights as digital masks. These masks were sent to a 1920×1080 resolution, 5um pixel-size, TI (Texas Instruments) manufactured DMD (Digital Micromirror Device) chip taken out from a commercial projector (Acer H5600). The chip was illuminated by a light source purchased from Hamamatsu with high intensity and peak wavelength around 365 nm. Between the DMD chip and the fabrication plane, a 10:1 composite lens from Carl-Zeiss with resolution of 1 micrometer was used to project image onto the resin surface to be cured. Each image exposed at the print-plane immediately solidified a layer at the top of the resin bath—the thickness of each layer is determined by the light penetration depth in the resin and the vertical step size of a three linear motion stage from Aerotech. The cured layer was then lowered to print the next layer. The process was repeated and the entire CAD model was fabricated in a layer-by-layer manner. A PDMS oxygen permeable window was used to control oxygen inhibition above the UV projection plane, maintaining a thin layer of uncured resin between the window and the cured sample throughout fabrication. A stitching operation was performed by controlling the stage motions in the XY direction to provide a large build size without compromising XY resolution. Horizontal fiber modules consisted of six 10 μm-thick support beam layers (40 μm wide beam diameters) and one 10 μm-thick fiber layer (4-20 μm wide fiber diameters), with exposure of 1.85 s/layer (poly(HDDA)-starPEG-high-E) or 2.6 s/layer (poly (HDDA)-starPEG-low-E). Vertical fibers or pillars consisted of seven 10 μm-thick layers (4-20 μm wide fiber diameters), with exposure of 1.85 s/layer (poly(HDDA)-starPEG-high-E) or 2.6 s/layer (poly(HDDA)-starPEG-low-E). Fibers were washed overnight in 100% ethanol, followed by at least 48 h in PBS. Washed fibers were sterilized under UV for 10 min inside the biosafety cabinet, rinsed once with sterile PBS, and stored for up to a month in PBS at 4° C. prior to functionalization. Fluorescent signal from dyes incorporated within fibers was strong for at least 1 month stored in PBS. Rhodamine B introduces noise in both green and blue channels of available confocal microscopy fluorescent filters, but remained below the signal of MBP and Hoechst stains used to identify myelin and oligodendrocyte cells; however, other dyes may be used.

Example 5: Fiber Functionalization

Before cell seeding, fibers were functionalized with one of three ligands: poly-D-lysine (PDL MW 70,000, Sigma), laminin (mouse natural laminin from Engelbreth-Holm-Swarm (EHS) sarcoma, Invitrogen), or fibronectin (from bovine plasma, Sigma). PDMS fibers: Fibers were washed in acetone (12 h) followed by wash in ethanol (12 h), to remove uncured species. After drying in the oven at 45° C. overnight, the PDMS fibers were activated in air plasma for 20 min to render them hydrophilic, followed by incubation with 100 mM (3-Aminopropyl)triethoxysilane (APTES, Sigma) at room temperature to introduce NH2 groups to the silicone surface, and washed three times with deionized water. The plates were incubated for 4 h at room temperature with a 1 mM solution of bis(sulfosuccinimidyl)suberate cross linker (BS3, Covach em) and 10 μg/mL ligand in HEPES buffer (50 mM, pH 8.0), followed by three washes with 1×phosphate buffer saline (PBS, pH 7.4). pHEMA fibers: Fibers incubated overnight with 100 μg/mL solution of ligand (fibronectin, laminin, or PDL) in 1×PBS. Poly(HDDA-co-starPEG)fibers: Fibers were incubated overnight in 50 μg/mL solution of ligand in 1×PBS, and subsequently washed three times with 1×PBS. The efficiency of ligand deposition was verified with 50 μg/mL fluorescently labeled poly-L-lysine (poly-L-lysine-FITC MW 15-30 kDa, Sigma) and laminin (Laminin-rhodamine, MW 225-400 kDa, Cytoskeleton). Coverslips were immobilized in 6-well plates using either high vacuum grease (Dow Corning) or a hydrophobic barrier pen (PAP pen, Vector Labs). Following functionalization, all fibers were washed once with SATO's medium and incubated for at least 1 h in proliferation medium before seeding. Murine OPCs were seeded at densities of ~25,000 cells/cm2.

Example 6: AFM-Enabled Nanoindentation and Rheology

The rheological properties of the pHEMA inks were determined using a controlled stress rheometer (DHR-3, TA Instruments, New Castle, Del., USA) fitted with a cone and plate geometry with a 40 mm diameter, 2° cone. Shear viscosity measurements were carried out in controlled shear stress (r) mode in a logarithmically ascending series of discrete steps. The elastic shear (G') and viscous (G") moduli. were measured using an oscillatory logarithmic stress sweep at a frequency of I Hz. Measurements are carried out at 22° C. using an aqueous solvent trap to mitigate drying effects. The Young's elastic modulus E was determined for fibers manufactured by both methods with all materials studied. Thin films of each material (10 μm thickness and width) fabricated by direct printing and PμSL using the same parameters as for artificial axons, and equilibrated overnight in PBS. Atomic force mjcroscope (AFM)-enabled nanoindentation measurements were conducted (MFP-3D Bio, Asylum Research) using cantilevers of nominal spring constant k=0.03 N/m terminating in a borosilicate spherical probe (Novascan) with an approximate diameter of 2 μm. The actual spring constant was calibrated via the thermal noise method. Between 10 and 20 force-depth responses were collected from one sample of each material, in PBS. For the most compliant materials, the cantilever base velocity was 1 μm/s and probe retraction was triggered after reaching a maximum force of 0.2 nN. For the stiffer materials (E>100 kPa) the cantilever base velocity was 1 μm/s and probe retraction was triggered after reaching a maximum force of 30-100 nN. Young's elastic moduli E were calculated by fitting the spherical Hertz model to a depth of 200 nm, or approximately 10% strain, and reported as ±s.e.m.

Example 7: Immunocytochemistry

Cells were fixed with 4% paraformaldehyde, washed with PBS, permeabilized with 0.1% Triton X-100 for 5 min, and blocked with 1% bovine serum albumin in PBS and 0.1% Triton-100 (blocking solution) for 1 h. Primary antibodies (rat anti-MBP, 1:200 dilution, Serotec) were diluted in blocking solution and incubated at room temperature for 1 h. Samples were washed 3 times with PBS and incubated with secondary antibodies (rabbit anti-rat IgG Alexa Fluor 488, 1:200 dilutions Invitrogen) in PBS for 1 h, followed by washing and staining of nuclei with Hoechst 33342 at a 1:1000 dilution for 5 min.

Example 8: Imaging, Data Acquisition, and Statistical Analysis

Phase contrast images were acquired with an inverted microscope (Olympus IX-81) equipped with an Orca-R2 camera. Fiber z-stacks were acquired with an inverted laser scanning confocal microscope (Olympus FVIOOO). Three-dimensional volumes were reconstructed from z-stacks using Fiji 3D Viewer; analysis of myelin segments and wrapping was done using the Volume Viewer plugin. The percentage of fully wrapped fibers (% FWF) was defined as the number of fibers wrapped around more than 80% of the fiber circumference, and presenting MBP+ segments extending longer than 30 μm along both the top and bottom of the fiber length. Statistical analysis was performed using two-tailed Student's t-test to determine statistical significance expressed as *p<0.05 compared between fiber coatings, with n=2 independent experiments.

Example 9: Fabrication of Artificial Axons

Fabrication of PDMS, pHEMA and poly(HDDA-co-starPEG) artificial axons was performed, as illustrated in FIGS. 4A-4L. Two types of inks for fiber production with extrusion-based 3D printing were optimized, including PDMS-based inks that form elastic and deformable fiber arrays and pHEMA-based inks that form viscoelastic hydrogels after hydration. In addition, new copolymer inks to achieve desired printing and cell compatibility properties via PµSL were created.

PDMS fibers with diameters of 10 µm, spanning lengths of 200 µm, and a Young's modulus E of 976±11 kPa were achieved (FIGS. 3, 4A, 4E, 4I). Fiber spacing and span length can be adjusted for desired parameters. The constructs measured 6×6 mm and typically consisted of one 10 µm thick layer of PDMS fibers with 30 µm distance between fiber centers, suspended on 200 µm thick PDMS beams with 200 µm spacing.

pHEMA inks were developed of different stiffness when hydrated in phosphate buffered saline. A relatively low stiffness ink (E=88±10 kPa) and a relatively high stiffness ink (E=333±30 kPa) were created (FIGS. 3, 4B, 4F, 4J). With these pHEMA inks, 3×3 mm multilayered log-pile arrays of overhanging fibers with diameters of 5 µm and 10 µm and adjustable interfiber spacing were printed, followed by UV-curing and stamping to a glass support using a PDMS rim (FIGS. 4B, 4F, 4J).

For PµSL techniques, the poly(HDDA-co-starPEG) material system was created to produce artificial axons that afford elastic moduli in the order of 0.1-200 kPa (FIG. 3A-B). Copolymerization of HDDA with biocompatible and compliant PEG polymer precursors was performed to mitigate the challenges that preclude HDDA implementation in biological applications (as discussed further in Example 13), while retaining capability of PµSL fabrication. A relatively high stiffness resin (E=140±35 kPa) and a very low stiffness resin (E=0.42±0.14 kPa) were created, resembling that of real axons. Overhanging fibers were fabricated with a uniform diameter from a range of 4-20 µm and suspended lengths spanning >100 µm, enabling physiological internode length for myelinating oligodendrocytes (FIGS. 4C, 4G, 4K). Compliant, vertically-oriented pillars were also fabricated with uniform diameters from a range of 4-20 µm and a pillar height of 70 µm (FIGS. 4D, 4H, 4I). The fibers and pillars were fabricated in modules of patterned arrays, with the printed fields measuring up to 1×1 mm, with total construct dimensions of 6×6 mm and an overall target sample thickness of 70-100 µm. The length, spacing, and diameter of printed cylinders in the fiber arrays and pillar arrays can be modified by adjusting the projection mask (FIGS. 4C and 4D).

Material composition and processing details of each of the above noted samples is shown in Table 1.

The fabricated samples of each material were examined by phase contrast microscope (FIGS. 4E, 4F, 4G, 4H). All fibers and pillars exhibited high fidelity and homogeneity across the arrays. The three-dimensionality and uniformity of the artificial axons was evaluated using confocal microscopy (FIGS. 4I, 4J, 4K, 4L).

Example 10: Adherence and Migration of OPCs Along Artificial Axons

Maturation of oligodendrocyte progenitor cells (OPCs) to myelinating oligodendrocytes (OLs) requires that OPCs migrate toward and engage axons in vivo, ultimately differentiating to OLs that encircle the axon diameter in myelin membrane that extends over 10 s of micrometers along the axon length.

As shown in FIGS. 5A-5L, it was confirmed that murine OPCs could adhere to, migrate along, and efficiently differentiate into myelinating oligodendrocytes on these artificial axons. Artificial axons were functionalized with either fibronectin, laminin, or poly-D-lysine (PDL) ligands, and murine OPCs were monitored throughout the experiments using phase contrast or fluorescence microscopy with live staining (or, alternatively, fluorescently reporting cell lines). OPCs adhered and adopted bipolar morphology, a marker of the progenitor stage, on artificial axons of all materials and coatings (FIG. 5A-5D). Using time-lapse imaging of life OPCs, cell migration along pHEMA artificial axons was recorded. On poly(HDDA-co-starPEG) mimetics, within minutes of seeding, cells adhered to the neuronal axon-mimicking fibers and spread slightly (See also Example 12, FIG. 11A). Within one day in proliferation medium, bipolar OPCs on laminin-coated fibers closely aligned with and engaged fibers with cell-generated processes (FIG. 5C); fewer OPCs exhibited bipolar morphology on fibers of the same diameter but coated with a nonspecific ligand (poly-D-lysine) within the same timeframe (See also Example 12, FIG. 11B).

Within the first two days in differentiation medium, OPCs acquired multipolar morphology and continued to mature for at least 20 days. Cell processes engaged multiple fibers in the adjacent proximity (FIG. 5E-5H). It was also observed that cell somas often spanned the empty space between two parallel fibers (See also Example 12, FIG. 11E, 11F). Some cells extended processes to fibers located up to 120 µm from the cell body (See also Example 12, FIG. 11D). In pillar

TABLE 1

Material composition of PDMS, pHEMA, and poly(HDDA-co-starPEG) samples

Figure 5C:
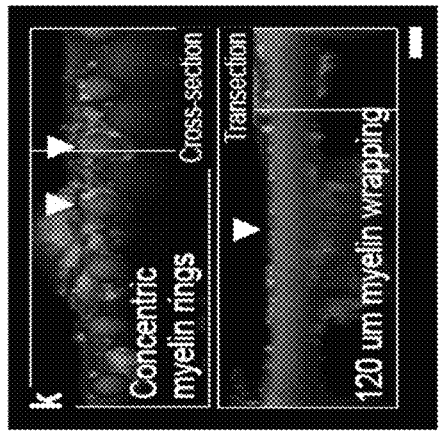
FIG. 5C is an image of OPC engagement, migration, and proliferation at day 1 after seeding on artificial axons fabricated in a horizontal configuration by PμSL. Scale bars are 100 μm.
Figure 5G:
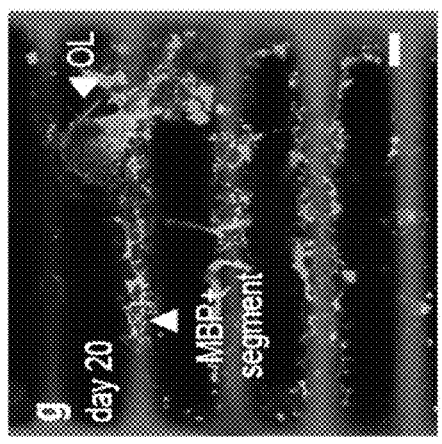
FIG. 5G is a plane view of oligodendrocyte differentiation and myelin wrapping on the artificial axons of FIG. 5C.
Figure 5K:
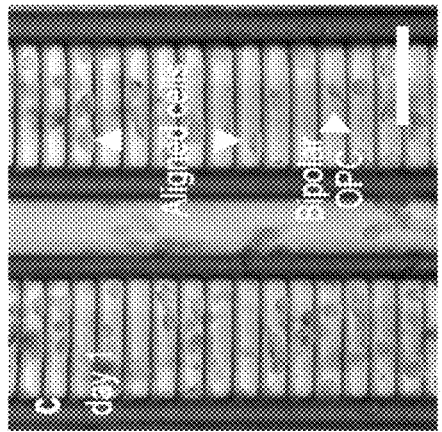
FIG. 5K is an image of cross- and trans-views of MBP positive myelin membrane around the artificial axons of FIG. 5C. Scale bars are 10 μm.
Figure 5D:
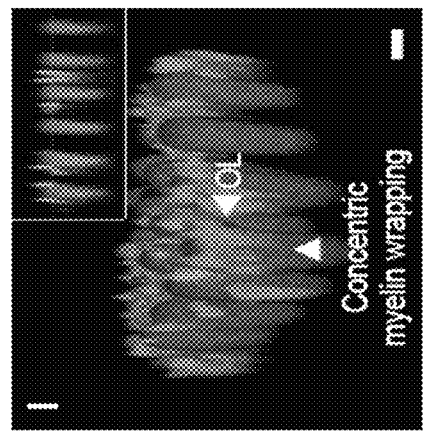
FIG. 5D is an image of OPC engagement, migration, and proliferation at day 1 after seeding on artificial axons fabricated in a vertical pillar configuration by PμSL. Scale bars are 100 μm.
Figure 5H:
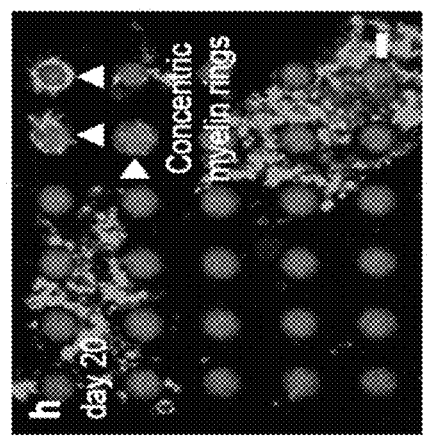
FIG. 5H is a plane view of oligodendrocyte differentiation and myelin wrapping on the artificial axons of FIG. 5D.
Figure 5L:
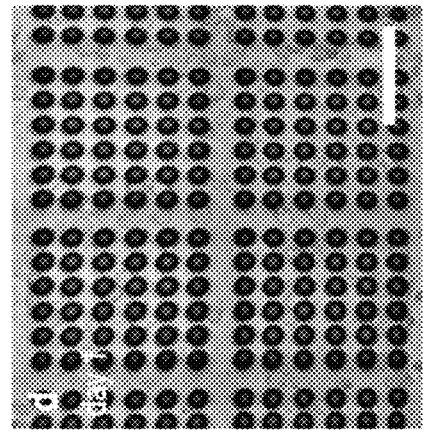
FIG. 5L is an image of cross- and trans-views of MBP positive myelin membrane around on the artificial axons of FIG. 5D. Scale bars are 10 μm.

|  | PDMS | Poly-HEMA Low E | Poly-HEMA High E | Poly(HDDA-co-starPEG) 3:1 | Poly(HDDA-co-starPEG) 1:1 |
| --- | --- | --- | --- | --- | --- |
| Base | SE1700: 90% w/w base, 10% w/w hardener | 10% pHEMA (1000 kDa) 25% pHEMA (300 kDa) 5% HEMA monomer 1% EGDMA (comonomer) | 10% pHEMA (1000 kDa) 25% pHEMA (300 kDa) 40% HEMA monomer 1% EGDMA (comonomer) | 30% w/w HDDA, 10% w/w starPEG | 10% w/w HDDA, 10% w/w starPEG |
| Curing Agent | Temperature 80° C. | 0.3% w/w Irgacure | 0.3% w/w Irgacure | 2% w/w Irgacure 819 | 2% w/w Irgacure 819 |
| Light Absorber | — | — | — | 0.7% Sudan I | 0.7% Sudan I |
| Fluorescent dye | 0.01% Rhodamine B | 0.01% Rhodamine B | 0.01% Rhodamine B | 0.1% Rhodamine B | 0.1% Rhodamine B |
| Solvent | — | 25% ethanol, 33.7% water | 23.5% water | DMSO | DMSO | arrays, cells adhered to pillar sides (FIG. 5L) and wrapped multiple pillars in the vicinity (FIG. 5H).

Concentric wrapping of membranes around the artificial axon perimeter and extending along the fiber length with immunostaining for myelin protein markers, such as myelin basic protein (MBP) around Rhodamine-B stained fibers (FIG. 5I-5L), was readily detected. Fully wrapped myelin segments ranged in segment length from <10 µm to entire artificial axon length (100-120 µm), as quantified by confocal fluorescence microscopy and image analysis (FIG. 5K). Using time-lapse fluorescence imaging of differentiated oligodendrocytes (six days in differentiation medium) expressing MBP-GFP, the dynamic deposition of MBP-positive membrane on pHEMA fibers was recorded.

Example 11: Controlled Variation of Artificial Axon Features and their Effect on Myelination The ability to independently manipulate characteristics of individual neuronal axon-mimicking fibers, fiber arrays, and the surrounding environment enables systematic interrogation of individual cues on oligodendrocyte response and myelination. To demonstrate this capacity for tunability, the following characteristics were varied: fiber diameter in horizontal and vertical arrays (FIG. 6A-6B, showing sample vertical arrays), mechanical stiffness of the fiber material (FIG. 6C-6D) and fiber surface coating (FIG. 6E-F) for arrays fabricated by PµSL. These variations were facilitated by modification of the digital masks, polymer precursor composition, or post-fabrication surface modification, respectively. Fiber diameters of 10 and 20 µm were achieved, and two levels of mechanical stiffness spanning three orders of magnitude (0.42±0.14 kPa and 140±35 kPa) were probed, while maintaining pillar aspect ratios of 1:3.5 and 1:7. Finally, the fiber surface chemistry was physically and chemically modified to express common ligands relevant to oligodendrocyte cell culture. The poly(HDDA-co-starPEG) fibers, as shown in FIGS. 6E-F, were sufficiently hydrophilic to enable a high extent of physisorption of common charged ligands, including poly-D-lysine (shown in green) and laminin (shown in red), that persisted for at least 20 days in culture.

Figure 6H:
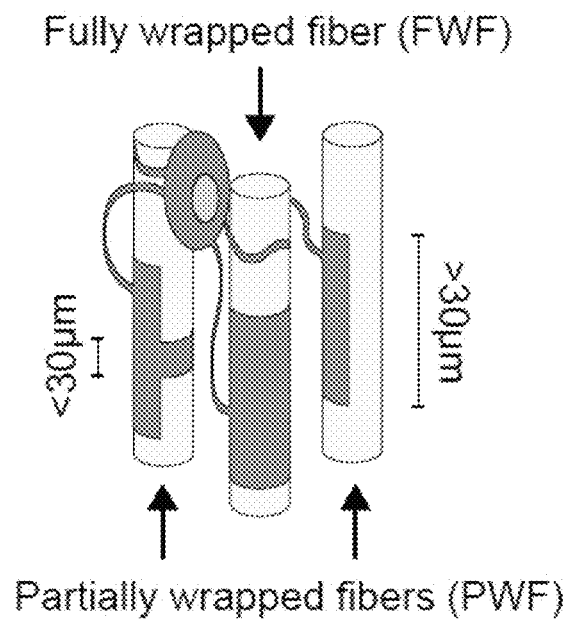
FIG. 6H is a schematic illustrating fully- and partially-wrapped fibers.

Confocal z-stacks of murine oligodendrocyte cultures at day 20, for fiber arrays with described above variations of fiber diameter, stiffness, and ligand coating, were acquired and the number of fibers exhibiting full wrapping, defined herein as concentric coverage of >80% MBP+ rings of segment length >30 µm along the fiber, were quantified (FIG. 6H). This comparison indicated significantly greater myelination (by ~3 fold) on smaller diameter fibers (10 µm vs 20 µm fibers), on stiffer fibers (140 kPa vs 0.4 kPa) and on laminin-coated fibers vs PDL-coated fibers (FIG. 6G). The increase on myelination on laminin coated artificial axons is consistent with previous findings for oligodendrocytes grown on very stiff electrospun fibers of ~1 µm diameter [11]. However, data herein can be acquired much more rapidly and reliably and on fibers of much lower (<1 kPa) stiffness reflecting physiological stiffness of biological axons. Rapid analysis is enabled by the high alignment of the fibers that facilitates automated quantification, and reliable identification of wrapping is enabled by the full view of the fiber circumference. A plan view can indicate some surface coverage but does not verify wrapping.

The artificial axon features within these arrays can also be varied as a function of position within the printed array, enabling design and fabrication of heterogeneous microenvironments with high precision.

Example 12: Gradients of Materials

Figure 7F:
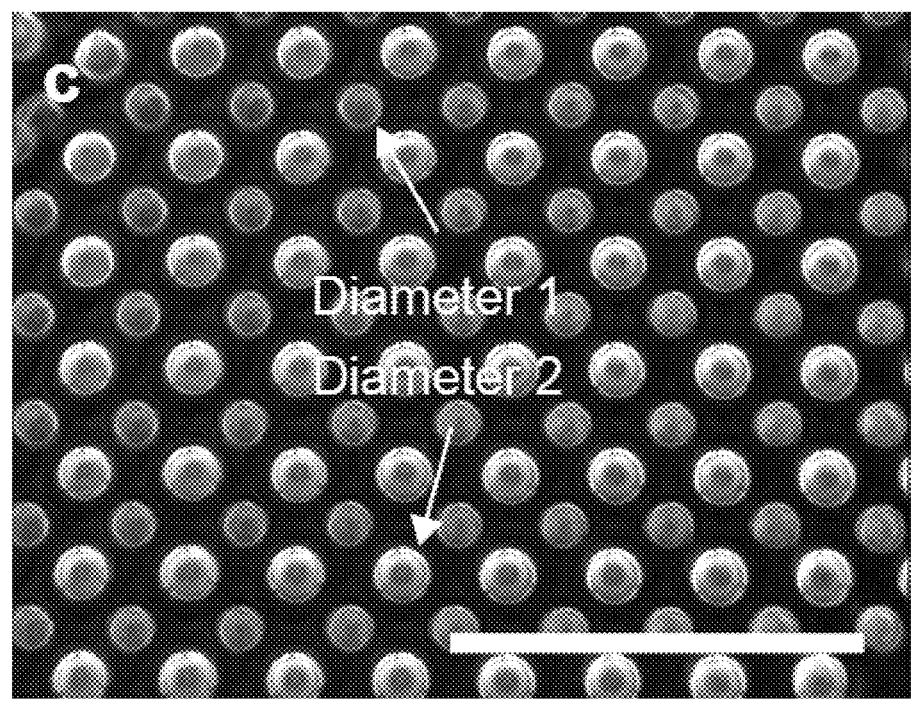
FIG. 7F is an image of poly(HDDA-co-starPEG) pillar arrangements including fibers of two diameters. Scale bars are 100 μm.
Figures 7G, 8A:
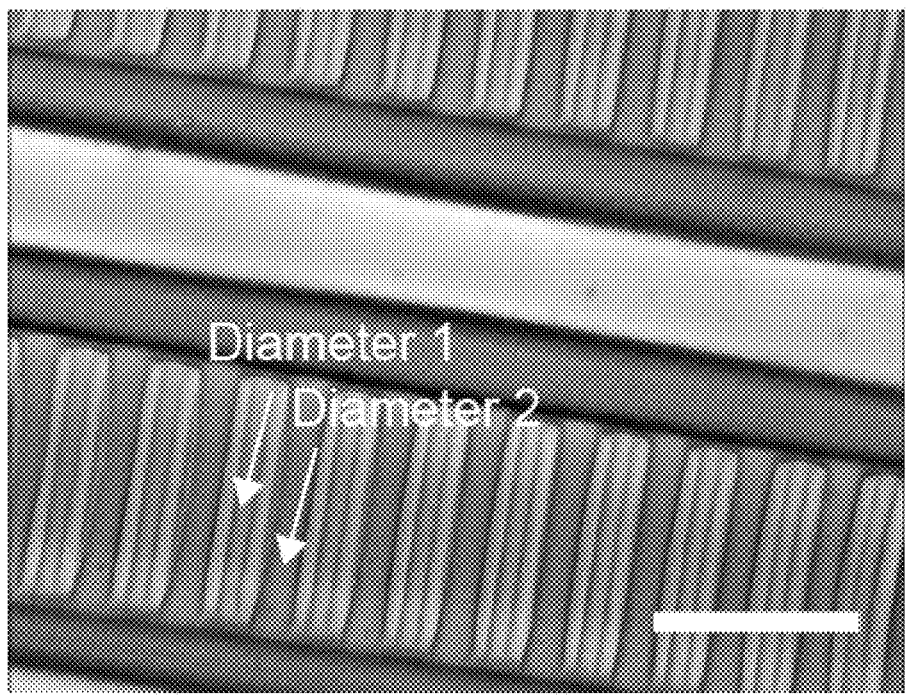
FIG. 7G is an image of poly(HDDA-co-starPEG) horizontal fiber arrangements including fibers of two diameters. Scale bars are 100 μm.
FIG. 8A is a table of compositions of the pHEMA inks used for the fabrication of the fibers of FIG. 7E.

Fiber bundles having complex architectures were created, as illustrated in FIGS. 7E-7G. Schematics are illustrated in FIGS. 7A-7D of examples of cell mimetics that include fibers with gradients of any of axon diameter, axon stiffness, and/or ligand concentration to mimic in vivo environments. Shown in FIG. 7E is a pHEMA fiber bundle comprising three distinct fiber inks corresponding to different stiffness (green=Ink 0; blue=Ink 1; purple=Ink 2, compositions and characteristics provided in FIGS. 8A-8C).

Shown in FIGS. 7F and 7G are arrangements of poly (HDDA-co-PEG) pillars and horizontal fibers, respectively, that include fibers of two different diameters. Spatial heterogeneity was achieved with PµSL techniques by digital mask modification. Multimaterial fabrication capability was included by flooding the resin bath with different photopolymer resins.

Figure 8B:
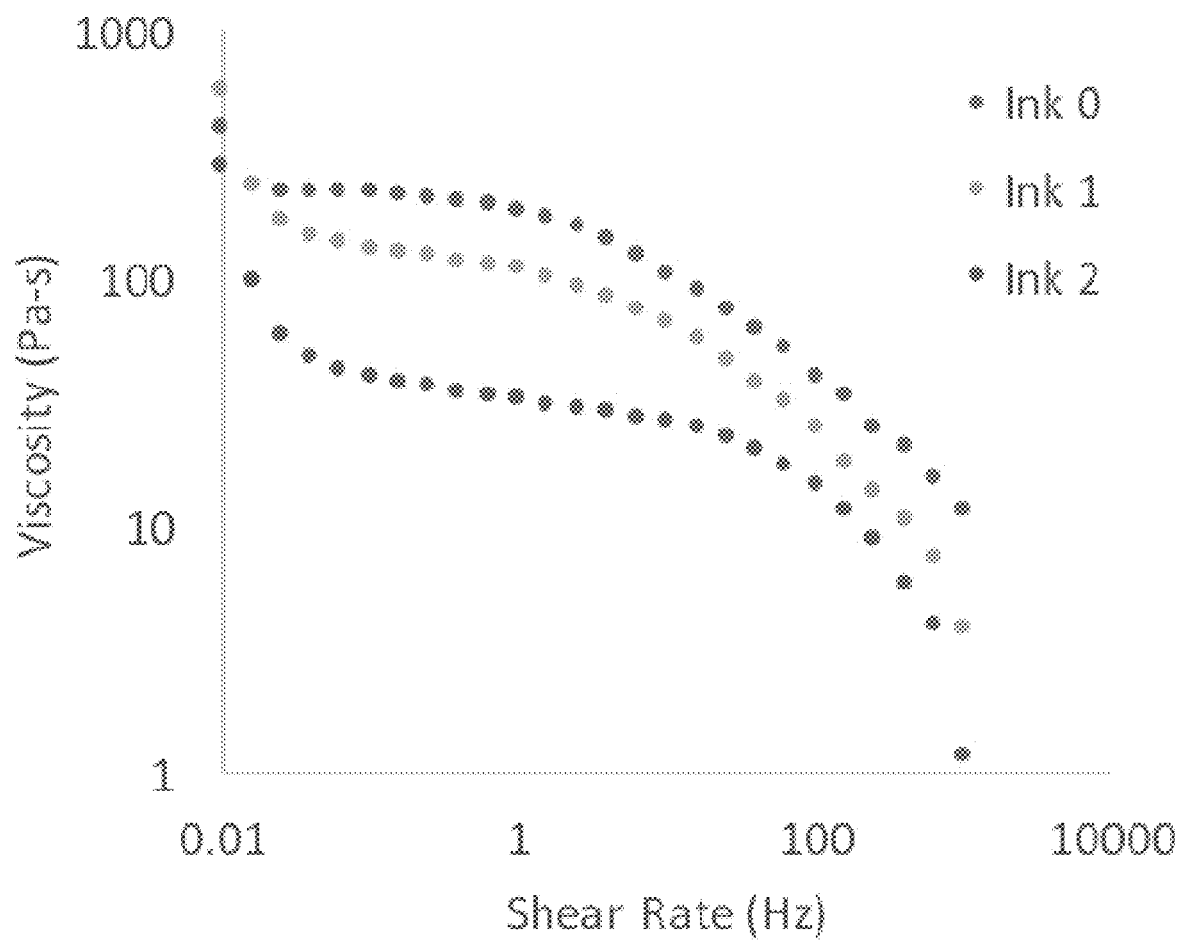
FIG. 8B is a chart illustrating viscosity versus shear rate of the pHEMA inks of FIG. 8A.
Figure 8C:
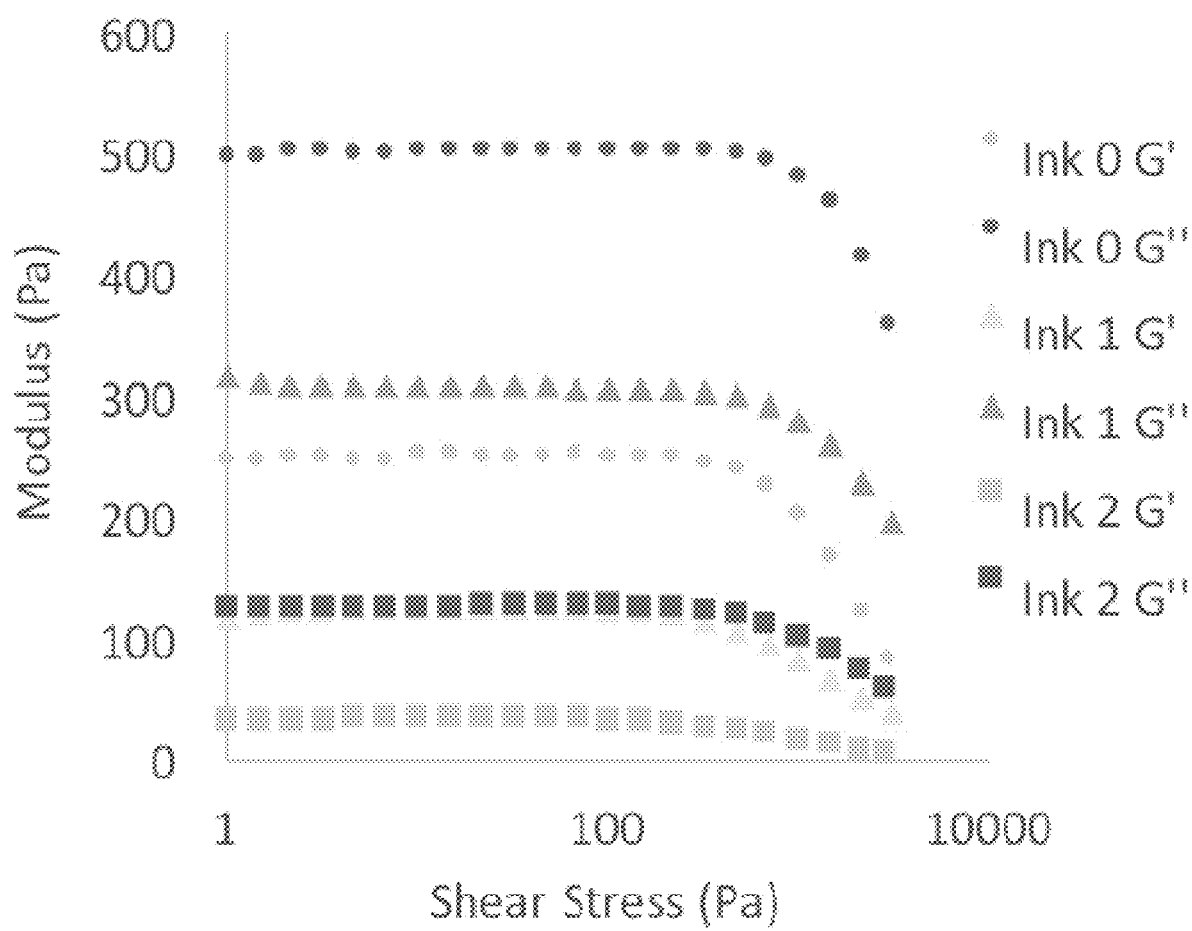
FIG. 8C is a chart illustrating modulus versus shear stress of the pHEMA inks of FIG. 8A.

The viscoelastic properties of the pHEMA inks of FIG. 7E are shown in FIGS. 8B and 8C. As shown in FIG. 8B, pHEMA inks exhibit viscosity drop with increasing shear rate. As shown in FIG. 8C, pHEMA inks exhibit shear thinning behavior at high shear stress.

Example 13: OPC Compatibility with HDDA Fibers

Figure 10A:
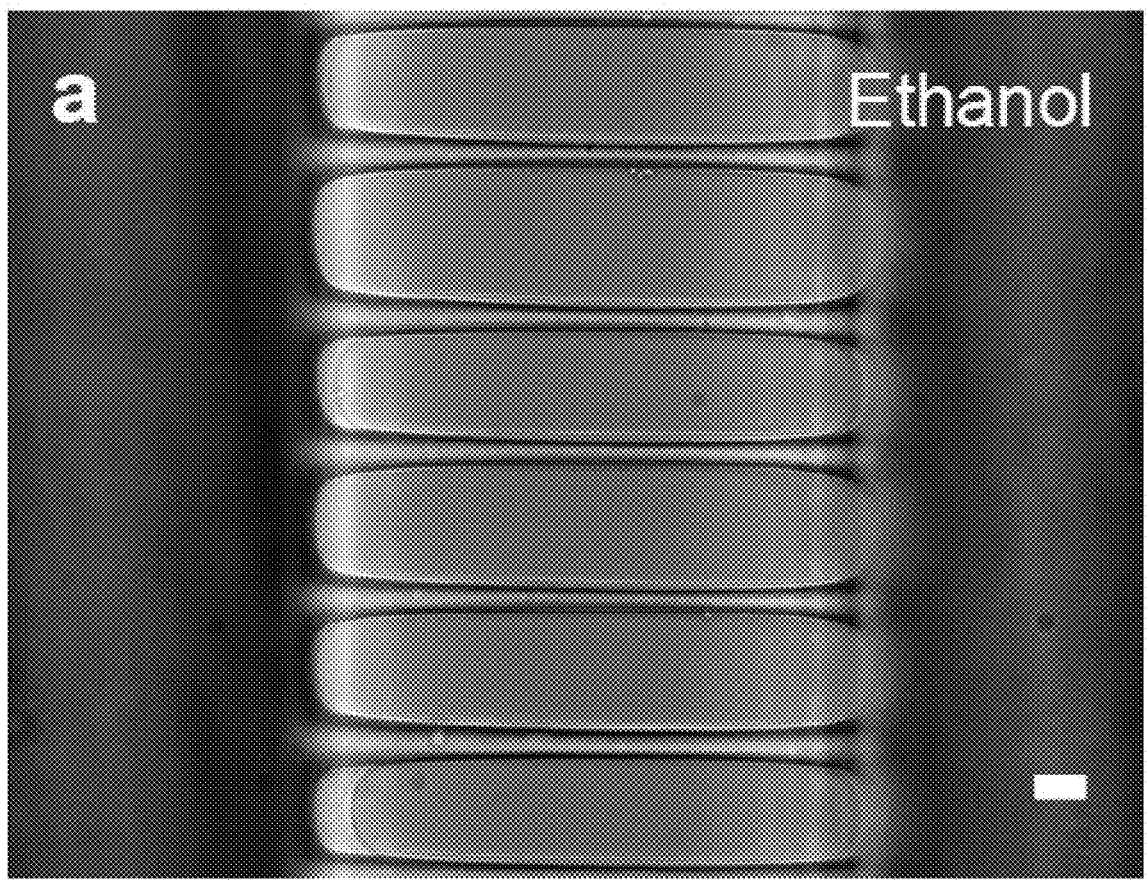
FIG. 10A is an image of HDDA fibers with diameters below 10 μm in ethanol. Scale bar is 10 μm.
Figure 10B:
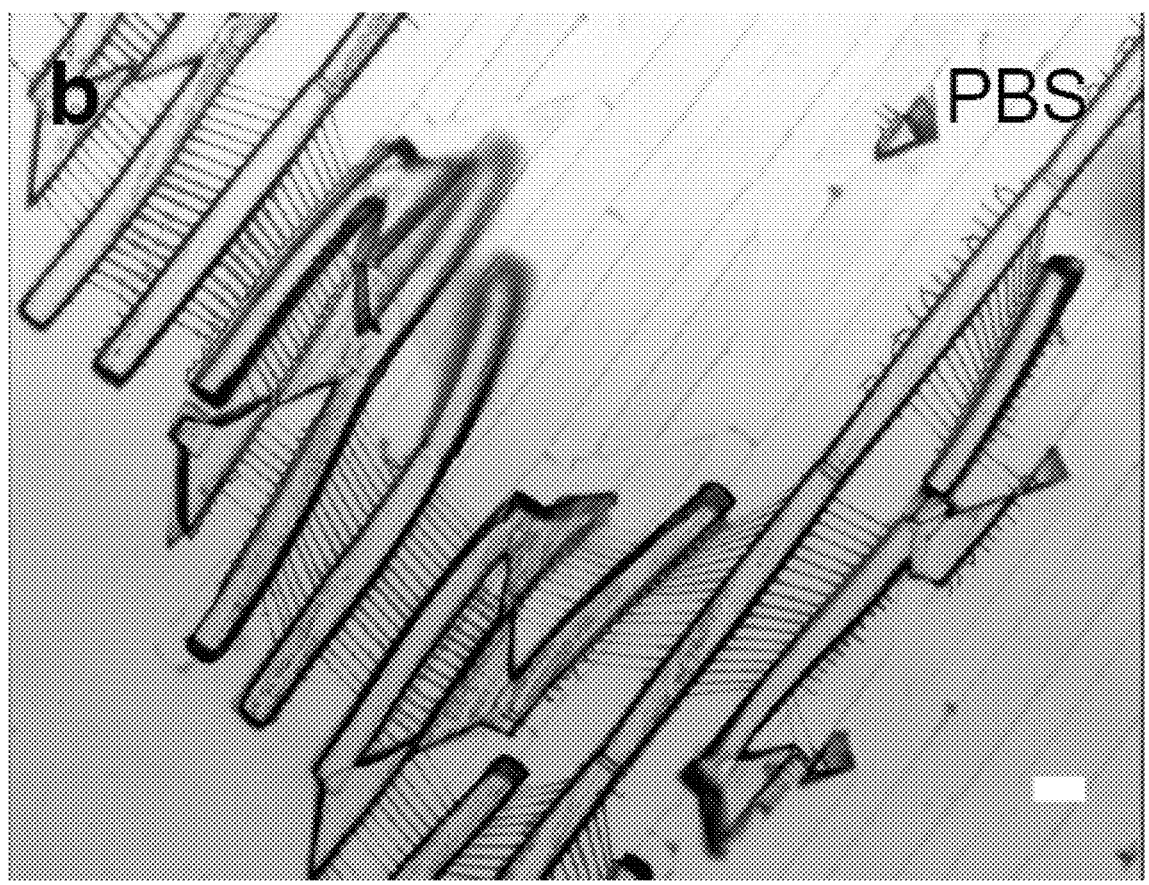
FIG. 10B is an image of HDDA fibers with diameters below 10 μm that peel off in a phosphate-buffered saline (PBS) solution. Scale bar is 100 μm.
Figure 10C:
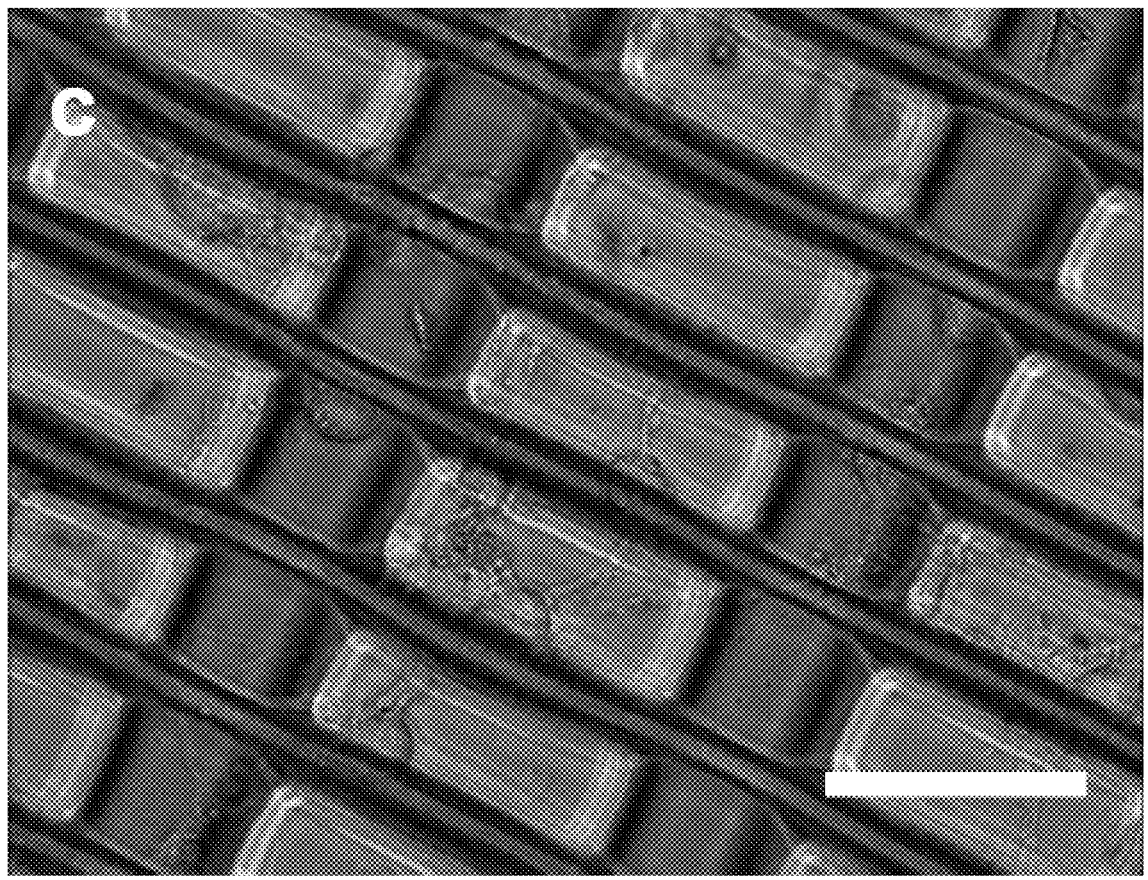
FIG. 10C is an image illustrating healthy OPCs on HDDA fibers. Scale bar is 100 μm.
Figure 10D:
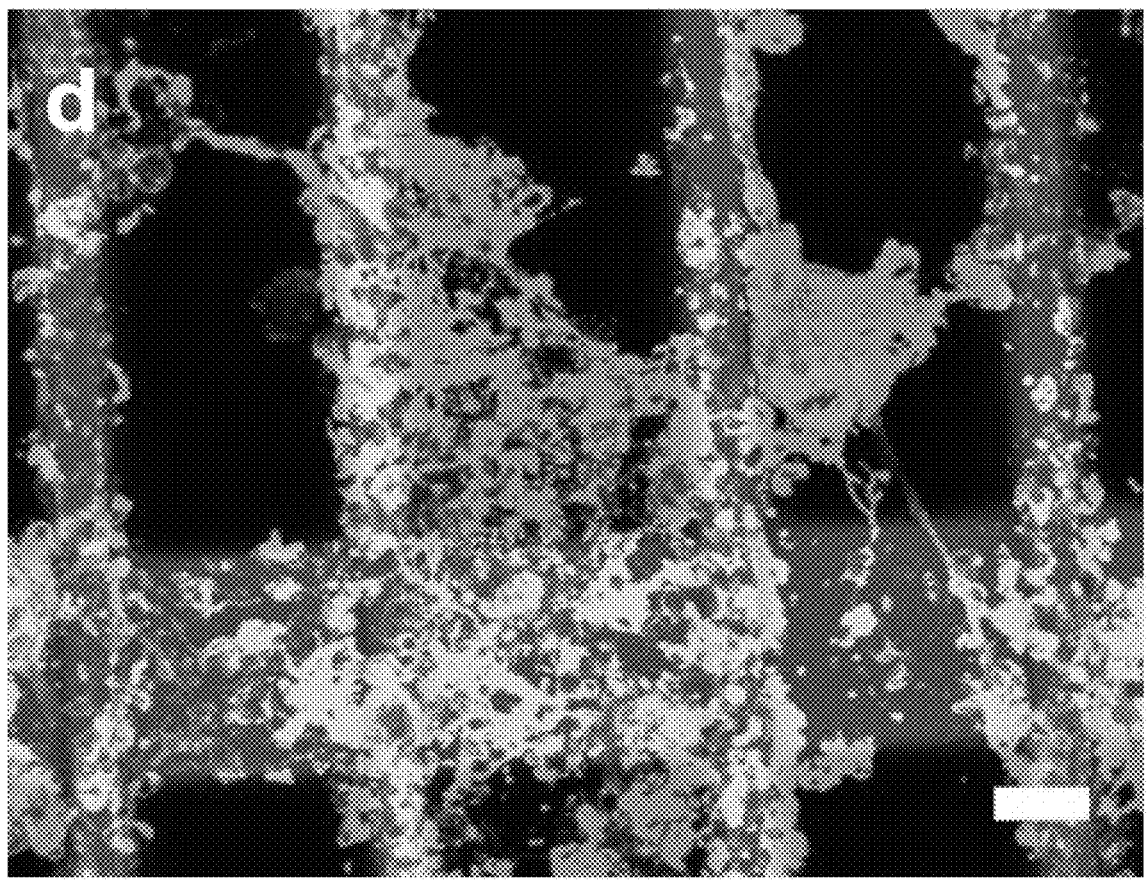
FIG. 10D is an image illustrating a compressed z-stack of HDDA fibers myelinated by mature oligodendrocytes. Scale bar is 10 μm.

HDDA fibers with diameters below 10 µm (FIG. 10A, 7 µm in the middle) were manufactured with PµSL and were shown to be stable in organic solvents (e.g., ethanol, acetone, isopropanol, DMSO). The HDDA fibers were incompatible with water, saline solutions (e.g., PBS) and biological medium in concentrations above 20-50% v/v in ethanol. As illustrated in FIG. 10B, the fibers, supports, and base layers break and peel or lift from the underlying functionalized glass substrate. Contrary to the incompatibility of murine OPCs with macroscopic (or bulk) HDDA substrates [29], and as illustrated in FIG. 10C, OPCs have better survival on HDDA microfibers and were shown to differentiate and engage with HDDA fibers extensively. A compressed z-stack of HDDA fibers myelinated by mature oligodendrocytes is shown in FIG. 10D.

Example 14: Effect of Fiber Surface Ligand on OPCs Biology

Figure 11A:
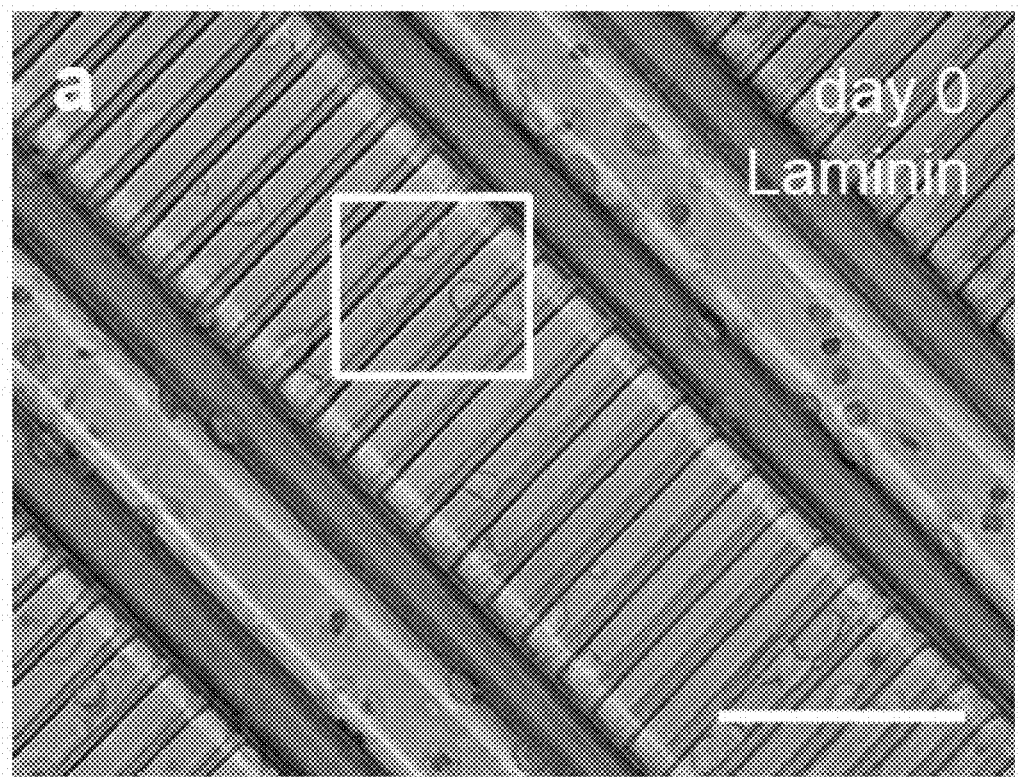
FIG. 11A is an image illustrating OPCs adherence to poly(HDDA-co-starPEG) fibers within one hour with flattened morphology.
Figure 11B:
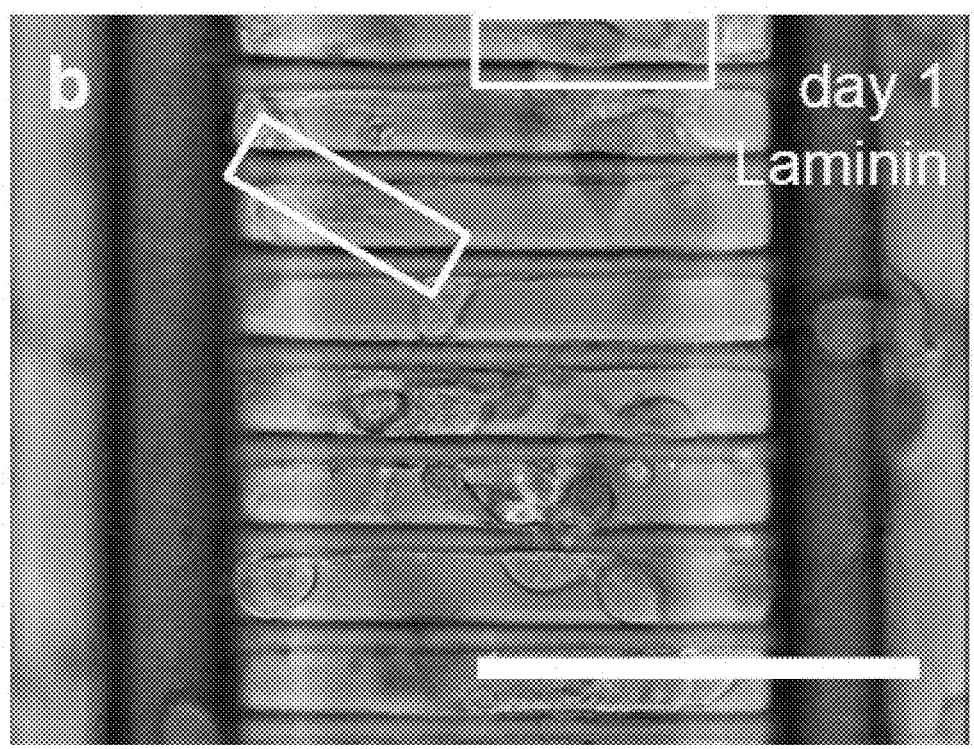
FIG. 11B is an image illustrating OPCs displaying bipolar morphology within one day in proliferation medium on laminin-coated poly(HDDA-co-starPEG) fibers.
Figure 11C:
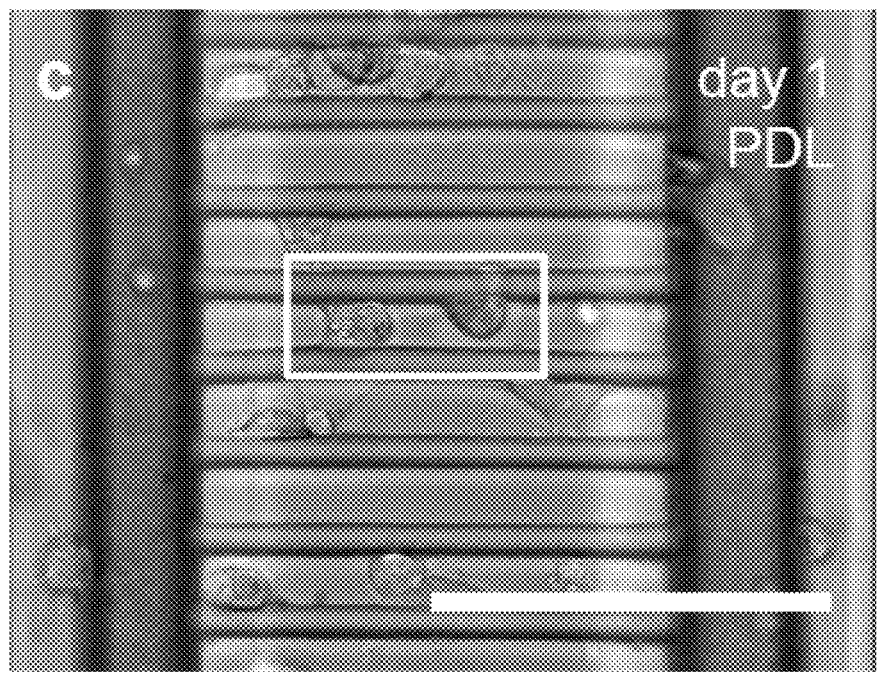
FIG. 11C is an image illustrating OPCs displaying less bipolar morphology and less processes within one day in proliferation medium on PDL-coated poly(HDDA-co-starPEG) fibers than on the laminin-coated fibers of FIG. 11B.

Murine OPC behavior on artificial axons fabricated with poly(HDDA-co-starPEG) was evaluated. As shown in FIG. 11A, cells adhered to poly(HDDA-co-starPEG) fibers functionalized with laminin within one hour with flattened morphology. Within one day, the cells displayed bipolar morphology on the laminin-coated poly(HDDA-co-starPEG) fibers in proliferation medium as illustrated in FIG. 11B. As shown in FIG. 11C, fewer cells displayed bipolar morphology and rather lacked processes within one day in proliferation medium on PDL-coated poly(HDDA-co-starPEG) fibers.

Figure 11D:
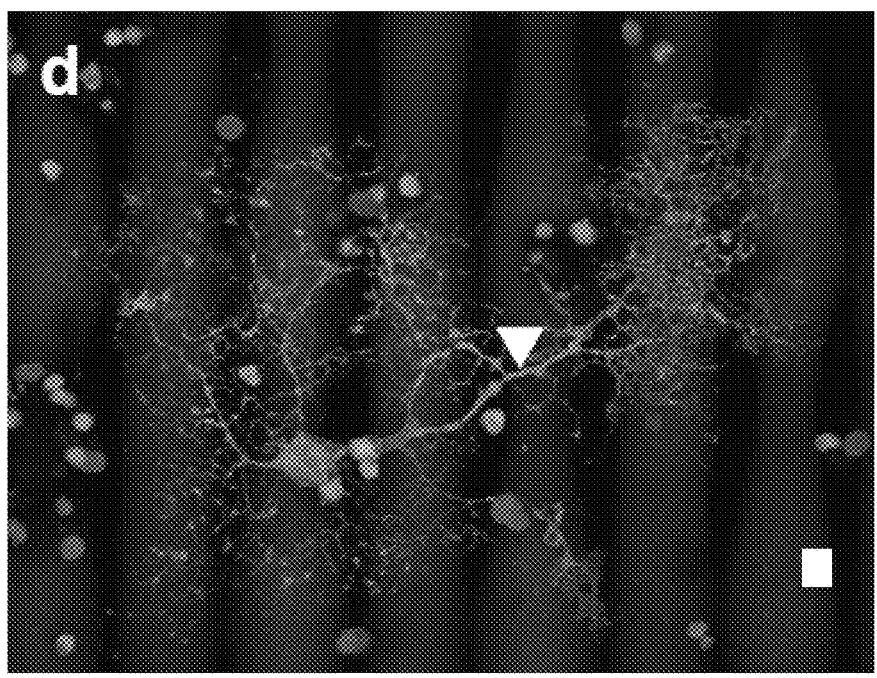
FIG. 11D is an image illustrating cells' extended processes to fibers located up to 120 μm from the cell body.
Figure 11E:
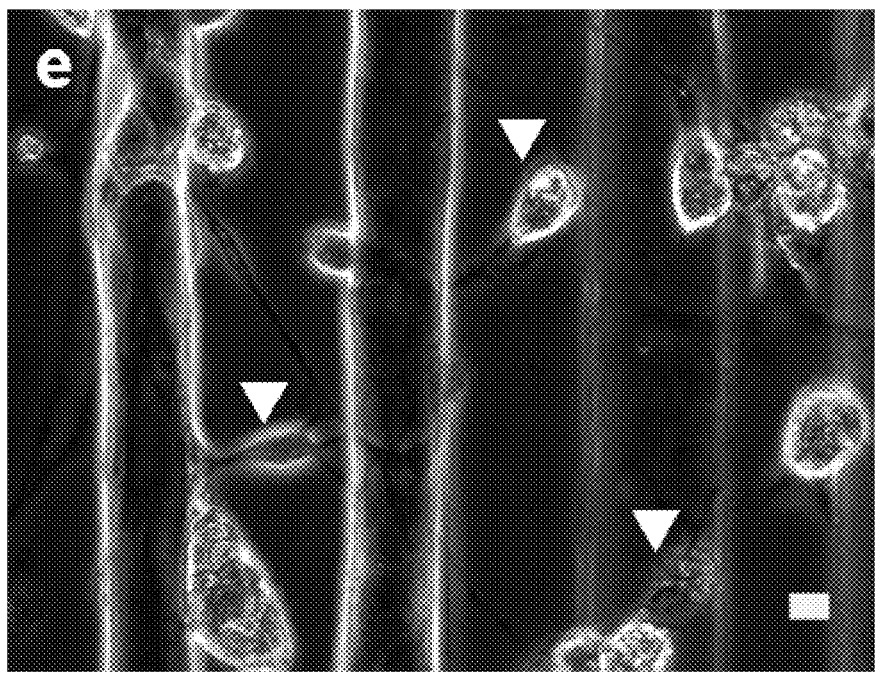
FIG. 11E is an image illustrating oligodendrocyte somas spanning space between parallel fibers.
Figure 11F:
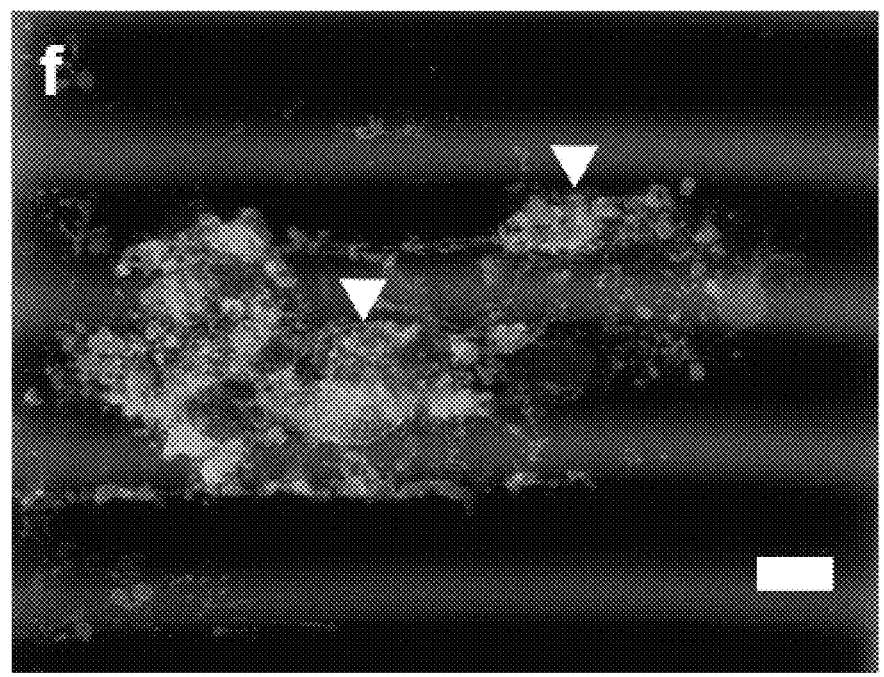
FIG. 11F is an image illustrating oligodendrocyte myelinating multiple fibers.
Figure 11G:
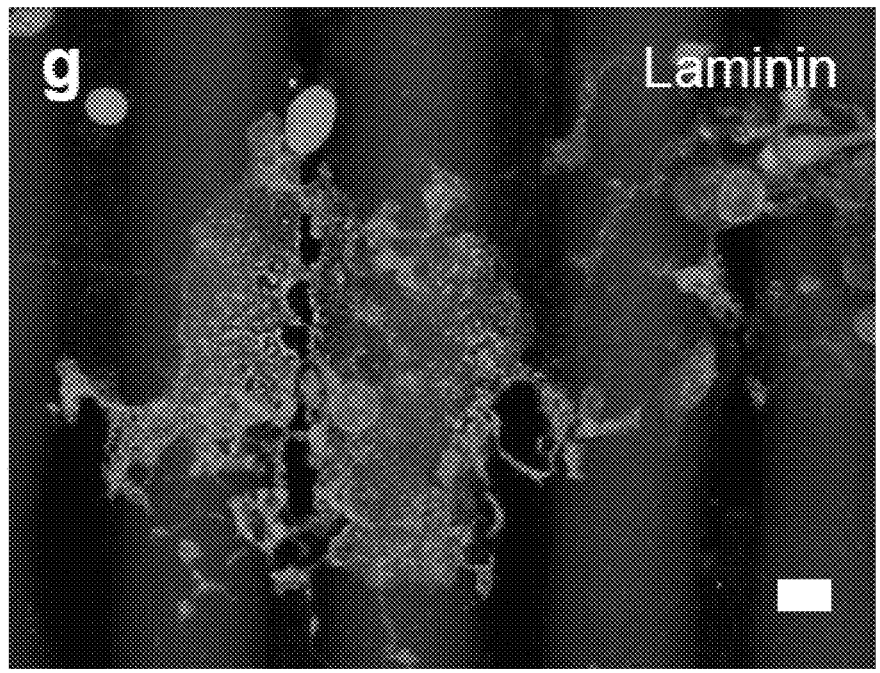
FIG. 11G is an image of laminin-coated PDMS fibers demonstrating a greater occurrence of membraneous cells than highly branched cells, as compared to fibronectin- and PDL-coated fibers (FIG. 11H, I).
Figure 11H:
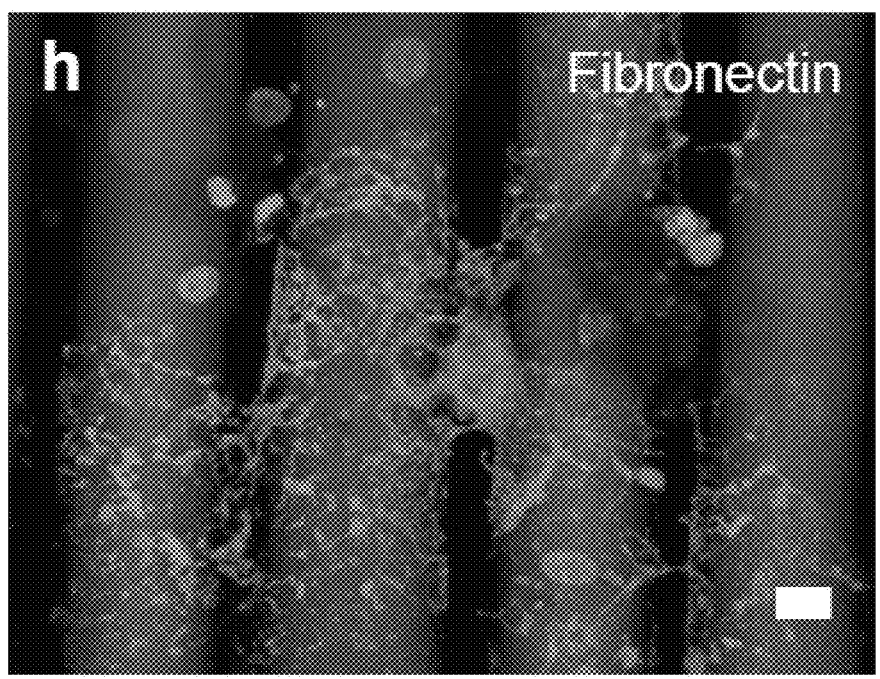
FIG. 11H is an image of fibronectin-coated PDMS fibers demonstrating a greater occurrence of long oligodendrocyte branches than membranous fibers.
Figure 11I:
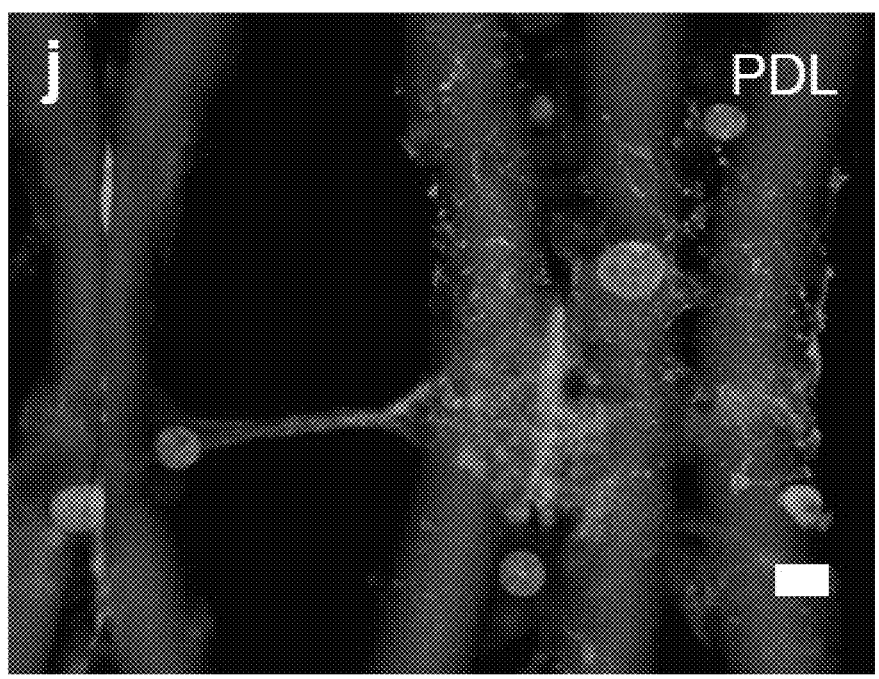
FIG. 11I is an image of PDL-coated PDMS fibers demonstrating a greater occurrence of long oligodendrocyte branches than membranous fibers.

Some cells extended process to fibers located up to 120 µm from the cell body (FIG. 11D). Oligodendrocyte somas often spanned the distance between parallel fibers, myelinating multiple fibers (FIGS. 11E-F).

There was a greater occurrence of membranous cells and fibers, rather than highly branched cells, on laminin-coated PDMS fibers, as compared with fibronectin and PDL coated artificial axons, in which a higher occurrence of long oligodendrocyte branches, rather than membranous fibers, was observed.

Figure 12A:
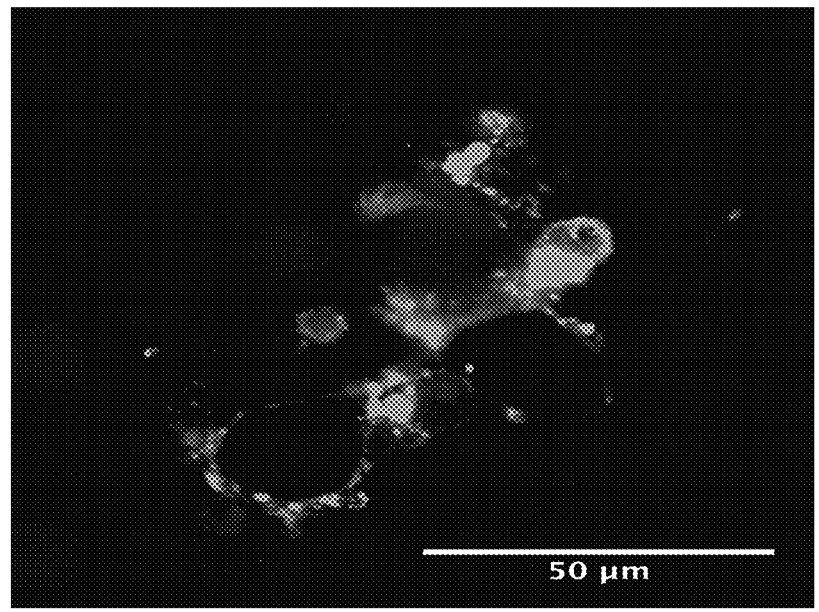
FIG. 12A is an image of human oligodendrocytes wrapping laminin-coated poly(HDDA-co-starPEG) pillar fibers with MBP-positive membrane (shown in green).
Figure 12B:
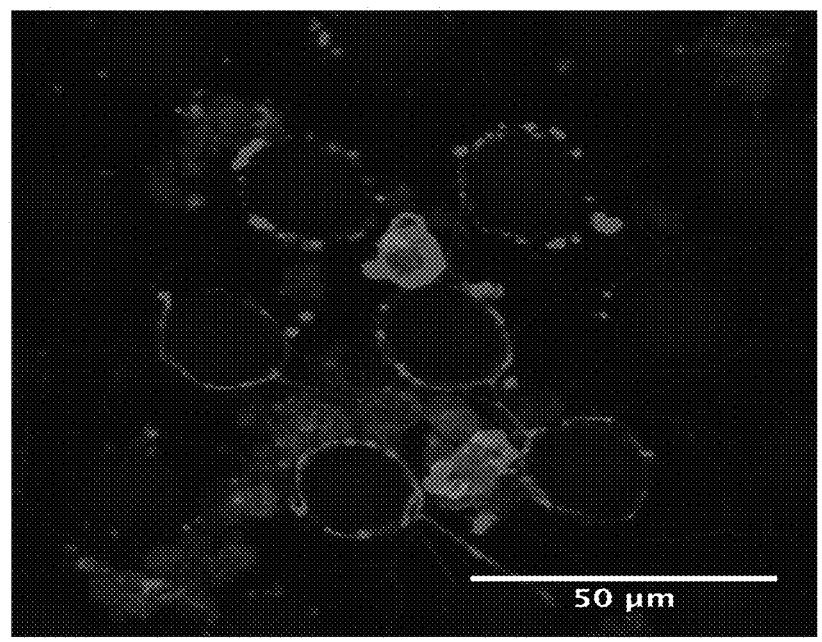
FIG. 12B is an image of human oligodendrocytes wrapping laminin-coated poly(HDDA-co-starPEG) pillar fibers with 04-positive membrane (shown in red).

Example 15: Human Oligodendrocytes Differentiate and Wrap Poly(HDDA-Co-starPEG) Pillars Human OPCs derived from human induced pluripotent stem cells were plated on poly(HDDA-co-starPEG) pillars with 15 µm diameter, coated with poly-ornithine and laminin. Cells adhered to the pillars, differentiated and wrapped pillars with MBP- (FIG. 12A) and O4-positive (FIG. 12B) membrane indicating myelination. This demonstrates compatibility of artificial axon platform with human origin glial cells.

REFERENCES

1 Espinosa-Hoyos, D., Jagielska, A., Homan, K. A., Du, H., Busbee, T., Anderson, D. G., Fang, N. X., Lewis, J. A., and Van Vliet, K. J., "Engineered 3D-printed artificial axons," Sci. Rep. 8. 478, 2018.
2 Franklin, R. J. M. Why does remyelination fail in multiple sclerosis? Nat. Rev. Neurosci. 3, 705-714 (2002).
3 Kohlschütter, A. & Eichler, F. Childhood leukodystrophies: a clinical perspective. Expert Rev. Neurother. 11, 1485-1496 (2011).
4 Wu, Y. et al. Alterations of myelin morphology and oligodendrocyte development in early stage of Alzheimer's disease mouse model. Neurosci. Lett. 642, 102-106 (2017).
5 Jarjour, A. a., Zhang, H., Bauer, N., ffrench-Constant, C. & Williams, A. In vitro modeling of central nervous system myelination and remyelination. Glia 60, 1-12 (2012)
6 Lariosa-Willingham, K. D. et al. Development of a central nervous system axonal myelination assay for high throughput screening. BMC Neurosci. 17, (2016)
7 Bullock, P. N. & Rome, L. H. Glass micro-fibers: a model system for study of early events in myelination. J. Neurosci. Res. 27, 383-393 (1990)
8 Howe, C. L. Coated Glass and Vicryl Microfibers as Artificial Axons. Cells Tissues Organs 183, 180-194 (2006)
9 Rosenberg, S. S., Kelland, E. E., Tokar, E., De la Torre, A. R. & Chan, J. R. The geometric and spatial constraints of the microenvironment induce oligodendrocyte differentiation. Proc. Natl. Acad. Sci. U.S.A. 105, 14662-14667 (2008)
10 Lee, S. et al. A culture system to study oligodendrocyte myelination processes using engineered nanofibers. Nat. Methods 9, 917-922 (2012)
11 Bechler, M. E., Byrne, L. & Ffrench-Constant, C. CNS Myelin Sheath Lengths Are an Intrinsic Property of Oligodendrocytes. Curr. Biol. 25, 2411-2416 (2015).
12 International Pub. No. WO2014/100190, "Micropillar Arrays for Assaying Myelination", Chan J. R., Lee, S.
13 Mei, F. et al. Micropillar arrays as a high-throughput screening platform for therapeutics in multiple sclerosis. Nat. Med. 20, 954-960 (2014).
14 Lu, Y.-B. et al. Viscoelastic properties of individual glial cells and neurons in the CNS. Proc. Natl. Acad. Sci. 103, 17759-17764 (2006).
15 Levental, I., Georges, P. C. & Janmey, P. A. Soft biological materials and their impact on cell function. Soft Matter 3, 299-306 (2007).
16 Christ, A. F. et al. Mechanical difference between white and gray matter in the rat cerebellum measured by scanning force microscopy. J. Biomech. 43, 2986-2992 (2010).
17 Jagielska, A. et al. Mechanical environment modulates biological properties of oligodendrocyte progenitor cells. Stem Cells Dev. 21, 2905-2914 (2012).
18 Streitberger, K.-J. et al. Brain viscoelasticity alteration in chronic-progressive multiple sclerosis. PLoS One 7, e29888 (2012)
19 Murphy, M. C. et al. Regional brain stiffness changes across the Alzheimer's disease spectrum. NeuroImage. Clin. 10, 283-290 (2016).
20 Liewald, D., Miller, R., Logothetis, N., Wagner, H.-J. & Schüz, A. Distribution of axon diameters in cortical white matter: an electron-microscopic study on three human brains and a macaque. Biol. Cybern. 108, 541-557 (2014).
21 Singh, V. et al. Scalable Fabrication of Low Elastic Modulus Polymeric Nanocarriers With Controlled Shapes for Diagnostics and Drug Delivery. J. Micro Nano-Manufacturing 3, 011002 (2014)
221 Gratson, G. M., Xu, M. & Lewis, J. A. Microperiodic structures: Direct writing of three-dimensional webs. Nature 428, 386-386 (2004).
23 Hanson Shepherd, J. N. et al. 3D microperiodic hydrogel scaffolds for robust neuronal cultures. Adv. Funct. Mater. 21, 47-54 (2011)
24 WO/2017/147501; PCT/US2017/019463 NEURONAL AXON MIMETICS FOR IN VITRO ANALYSIS OF NEUROLOGICAL DISEASES, MYELINATION, AND DRUG SCREENING; Aug. 31, 2017. Jagielska A., Van Vliet K. J., Homan K., Busbee T. A., Lewis J. A.
25 Sun, C., Fang, N., Wu, D. M. & Zhang, X. Projection micro-☐stereolithography using digital micro-mirror dynamic mask. Sensors Actuators, A Phys. 121, 113-120 (2005).
26 Baker, S. R., Banerjee, S., Bonin, K. & Guthold, M. Determining the mechanical properties of electrospun poly-ε-caprolactone (PCL) nanofibers using AFM and a novel fiber anchoring technique. Mater. Sci. Eng. C 59, 203-212 (2016)
27 Liu, C., Wong, H. M., Yeung, K. W. K. & Tjong, S. C. Novel electrospun polylactic acid nanocomposite fiber mats with hybrid graphene oxide and nanohydroxyapatite reinforcements having enhanced biocompatibility. Polymers (Basel). 8, (287-306 (2016).
28 Hardin, J. O., Ober, T. J., Valentine, A. D. & Lewis, J. A. Microfluidic printheads for multimaterial 3D printing of viscoelastic inks. Adv. Mater. 27, 3279-3284 (2015).
29 Espinosa-Hoyos, D., Du, H., Fang, N. X. & Van Vliet, K. J. Poly(HDDA)-Based Polymers for Microfabrication and Mechanobiology. MRS Adv. (2017).
30 Schregel, K. et al. Demyelination reduces brain parenchymal stiffness quantified in vivo by magnetic resonance elastography. Proc. Natl. Acad. Sci. 109, 6650-6655 (2012).
31 Friese, M. A. et al. Acid-sensing ion channel-1 contributes to axonal degeneration in autoimmune inflammation of the central nervous system. Nat. Med. 13, 1483-1489 (2007).
32 Jagielska, A., Wilhite, K. D. & Van Vliet, K. J. Extracellular acidic pH inhibits oligodendrocyte precursor viability, migration, and differentiation. PLoS One 8, e76048 (2013).
33 Harlow, D. E. & Macklin, W. B. Inhibitors of myelination: ECM changes, CSPGs and PTPs. Exp. Neurol. 251, 39-46 (2014).

34 Jagielska, A. et al. Mechanical strain promotes oligodendrocyte differentiation by global changes of gene expression. Front. Cell. Neurosci. 11, 93 (2017).

While example embodiments have been particularly shown and described, it will be understood by those skilled in the art that various changes in form and details may be made therein without departing from the scope of the embodiments encompassed by the appended claims.

What is claimed is:

1. A cell-mimetic device comprising:
an array of fibers comprised of a material comprising:
hexanediol diacrylate (HDDA); and
at least one of PEG-acrylate, PEG-diacrylate, and a multi-arm PEG-acrylate, wherein at least a subset of the array of fibers is free-standing pillars.

2. The cell-mimetic device of claim 1, wherein the free-standing pillars have a pillar height of about 10 µm to about 1000 µm.

3. The cell-mimetic device of claim 1, wherein the free-standing pillars have a pillar height of about 20 µm to about 100 µm.

4. The cell-mimetic device of claim 1, wherein the material comprises poly(HDDA-co-starPEG).

5. The cell-mimetic device of claim 4, wherein the poly(HDDA-co-starPEG) material comprises about 1% to about 99% w/w HDDA.

6. The cell-mimetic device of claim 5, wherein the poly(HDDA-co-starPEG) material comprises about 5% to about 50% w/w HDDA.

7. The cell-mimetic device of claim 5, wherein the poly(HDDA-co-starPEG) material comprises about 5% to about 35% w/w HDDA.

8. The cell-mimetic device of claim 5, wherein the poly(HDDA-co-starPEG) material comprises about 10% to about 30% w/w HDDA.

9. The cell-mimetic device of claim 1, wherein the fibers have a post-curing stiffness of between about 0.1 and 200 kPa.

10. The cell-mimetic device of claim 9, wherein the fibers have a post-curing stiffness of between about 0.1 kPa and 50 kPa.

11. The cell-mimetic device of claim 9, wherein the fibers have a post-curing stiffness of between about 0.1 kPa and 10 kPa.

12. The cell-mimetic device of claim 9, wherein the fibers have a post-curing stiffness of between about 0.1 kPa and 1 kPa.

13. The cell-mimetic device of claim 1, wherein the fibers have diameters between about 0.1 µm to 20 µm.

14. The cell-mimetic device of claim 13, wherein the fibers have diameters between about 1 µm to 20 µm.

15. The cell-mimetic device of claim 1, wherein at least a subset of the fibers are arranged in a horizontal configuration.

16. The cell-mimetic device of any of claim 15 wherein the subset of fibers in the horizontal configuration each include a suspended portion.

17. The cell-mimetic device of claim 16 wherein the subset of fibers are suspended between supports at a distance of about 0.5 µm to about 1000 µm.

18. The cell-mimetic device of claim 16 wherein the subset of fibers are suspended between supports at a distance of about 10 µm to about 200 µm.

19. The cell-mimetic device of claim 1, wherein the fibers are modified by a surface ligand.

20. The cell-mimetic device of claim 1, wherein the array of fibers is arranged in a three-dimensional (3D) structure comprising fibers having cylindrically exposed portions.

21. An assay method comprising:
contacting the device recited in claim 1 with at least one population of cells; and studying at least one feature of an interaction of the at least one population of cells with at least one of: (a) the device, (b) a molecular compound, a drug or active pharmaceutical ingredient, and (c) another population of cells.

22. An assay method of claim 21 wherein fibers represent neuronal axons and studied interactions between cells and fibers comprise neural cell differentiation and myelination, for animal or human origin cells.

23. A method of manufacturing the cell mimetic device of claim 1 comprising a Projected Microstereolithography method.

24. A method of manufacturing the cell mimetic device of claim 1, comprising:
generating a series of digital images of a microstereolithography mask;
sequentially projecting the images, illuminated by a light source, onto a resin bath comprising a material comprising hexanediol diacrylate (HDDA) and at least one of PEG-acrylate, PEG-diacrylate, and a multi-arm PEG-acrylate; and
causing an exposed portion of the material to cure, the cured material forming the array of fibers of the cell-mimetic device.

25. The method of claim 24, wherein the array includes fibers arranged in a horizontal configuration.

26. The method of claim 25, wherein at least a subset of the fibers in the horizontal configuration each include a suspended portion.

27. The method of claim 24, wherein the array includes fibers arranged in a vertical or tilted configuration.

* * * * *